US010112895B2

(12) United States Patent
Ricciardi et al.

(10) Patent No.: US 10,112,895 B2
(45) Date of Patent: Oct. 30, 2018

(54) ANTIVIRALS AGAINST MOLLUSCUM CONTAGIOSUM VIRUS

(71) Applicant: THE TRUSTEES OF THE UNIVERSITY OF PENNSYLVANIA, Philadelphia, PA (US)

(72) Inventors: Robert P. Ricciardi, East Marlborough, PA (US); Allen B. Reitz, Lansdale, PA (US); Michael H. Parker, Chalfont, PA (US); Simon David Peter Baugh, Ringoes, NJ (US); Manunya Nuth, Philadelphia, PA (US); Hancheng Guan, Downingtown, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/515,534

(22) PCT Filed: Sep. 28, 2015

(86) PCT No.: PCT/US2015/052700

§ 371 (c)(1),
(2) Date: Mar. 29, 2017

(87) PCT Pub. No.: WO2016/053893

PCT Pub. Date: Apr. 7, 2016

(65) Prior Publication Data

US 2017/0217882 A1 Aug. 3, 2017

Related U.S. Application Data

(60) Provisional application No. 62/057,029, filed on Sep. 29, 2014.

(51) Int. Cl.

| | |
|---|---|
| *C07C 311/39* | (2006.01) |
| *C07C 217/58* | (2006.01) |
| *C07D 231/56* | (2006.01) |
| *C07D 263/32* | (2006.01) |
| *C07D 235/26* | (2006.01) |
| *A61K 31/136* | (2006.01) |
| *A61K 31/221* | (2006.01) |
| *A61K 31/4166* | (2006.01) |
| *A61K 31/44* | (2006.01) |

(52) U.S. Cl.

CPC .......... *C07C 311/39* (2013.01); *C07C 217/58* (2013.01); *C07D 231/56* (2013.01); *C07D 235/26* (2013.01); *C07D 263/32* (2013.01)

(58) Field of Classification Search

None

See application file for complete search history.

(56) References Cited

FOREIGN PATENT DOCUMENTS

WO 2013059559 A2 4/2013

OTHER PUBLICATIONS

Schormann, et al., Antimicrobial Agents and Chemotherapy, 55:5054. (Year: 2011).*

Achenbach, et al., Med. Chem. Commun., 4:920. (Year: 2013).*

Congreve, et al., J. Med. Chem., 50:1124. (Year: 2007).*

International Search Report and Written Opinion for PCT International Application No. PCT/US2015/052700.

Pubchem, Substance Record for SID 6798514, create date: Sep. 16, 2005, retrieved from internet on Oct. 27, 2015, https://pubchem.ncbi.nlm.nih.gov/substance/6798514/version/1#section=Top.

Deng, et al., "Identification of Small Molecule Sphingomyelin Synthase Inhibitors", European Journal of Medicinal Chemistry, vol. 73, 2014, pp. 1-7.

Extended European Search Report for European Patent Application No. 15845622.8 dated Apr. 24, 2018.

Guan, et al., A novel target and approach for identifying antivirals against molluscum contagiosum virus, Antimicrobial Agents and Chemotherapy 20(12) ,2014 ,7383-7389.

Nuth, et al.,Identification of Inhibitors that Block Vaccinia Virus Infection by Targeting the DNA Synthesis Processivity Factor D4, Journal of Medicinal Chemistry 54(9) ,2011 ,3260-3267.

Schormann, et al., A novel target and approach for identifying antivirals against molluscum contagiosum virus, Antimicrobial Agents and Chemotherapy 55(11) ,2011 ,5054-5062.

* cited by examiner

*Primary Examiner* — Michael Barker

(74) *Attorney, Agent, or Firm* — Saul Ewing Arnstein & Lehr LLP; Kathryn Doyle; Domingos J. Silva

(57) ABSTRACT

This invention provides compounds of formulas (I)-(XIV) as defined in the specification, and pharmaceutical compositions comprising the same, and methods of inhibiting, treating, or abrogating a molluscum contagiosum virus infection in a subject using compounds or compositions of the invention:

(I)

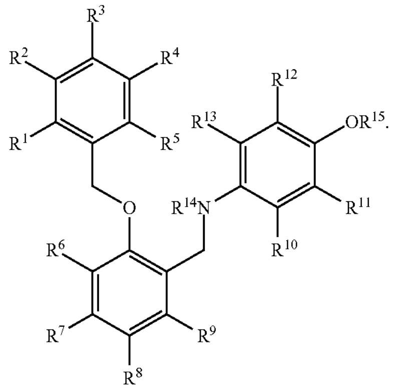

16 Claims, 16 Drawing Sheets

Specification includes a Sequence Listing.

Cmpd 10 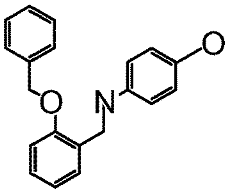
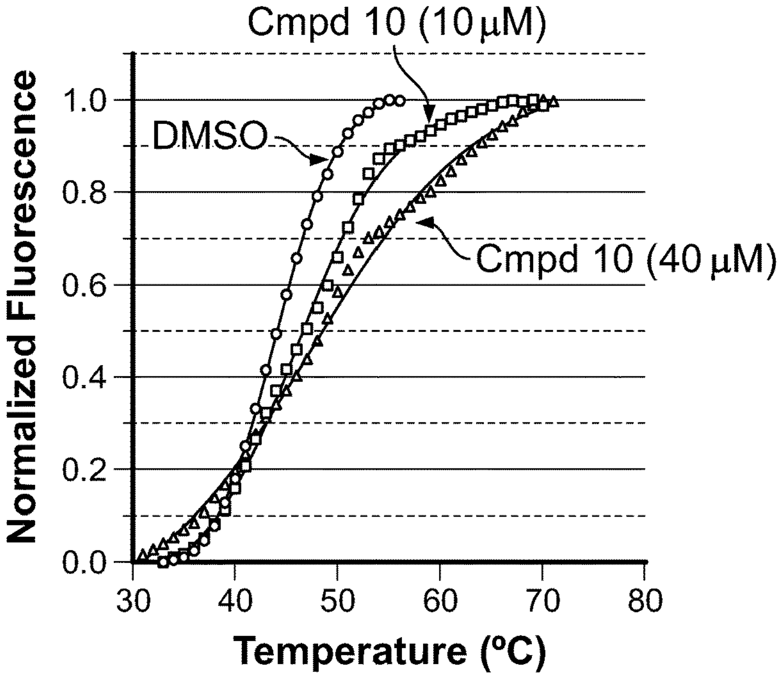
FIG. 5A
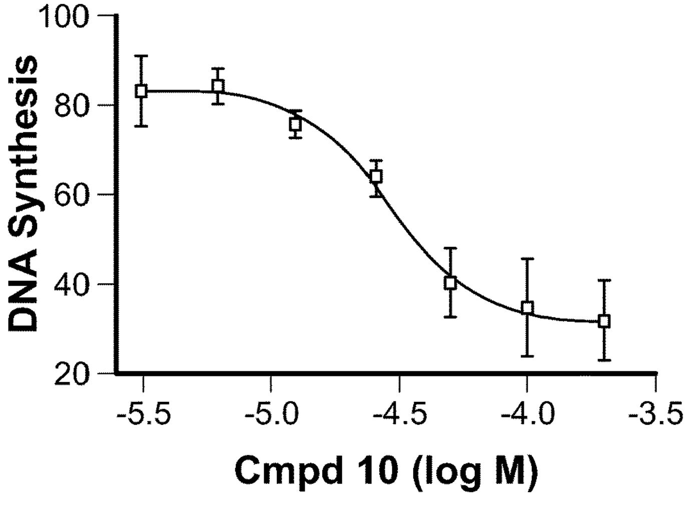
FIG. 5B

```
mD4   1 MLRERALRAAPHVLRYHEDWEPVAEPLADAYAEVAPWLLRDRTEPAPERFFRQLELPLRD
vD4   1 MNSVTVSH-APYTITYHDDWEPVMSQLVEFYNEVASWLLRDETSPIPDKFFIQLKQPLRN

mD4  61 KRVCIVGIDPYPEGATGVPFESPDFSKKTARALAAAARAAEHGGCRRVSAYRNYDFRGV
vD4  60 KRVCVCGIDPYPKDGTGVPFESPNFTKKSIKEIASSISRLTG------VIDYKGYNLNII

mD4 121 QGVLAWNYYLSCRRGETKSHAMHWERIARMLLAHIARFVRVFYFLGRSDFGGVRAKLTAP
vD4 114 DGVIPWNYYLSCKLGETKSHAIYWDKISKLLLQHITKHVSVLYCLGKTDFSNIRAKIESP

mD4 181 VTLLVGYHPAARGGQFESERTLEILNVLLELHGLAPVDWAQGFVPL 226
vD4 174 VTTIVGYHPAARDRQFEKDRSFEIINVLLELDNKAPINWAQGFIY 218
```

FIG. 9A

FIG. 9B

ANTIVIRALS AGAINST MOLLUSCUM CONTAGIOSUM VIRUS

CROSS-REFERENCE TO RELATED APPLICATIONS

The present application is a 35 U.S.C. § 371 national phase application from, and claims priority to, International Application No. PCT/US2015/052700, filed Sept. 28, 2015, and published under PCT Article 21(2) in English, which claims priority under 35 U.S.C. § 119(e) to U.S. Provisional Application No. 62/057,029, filed Sept. 29, 2014, all of which applications are incorporated herein by reference in their entireties.

STATEMANT REGARDING FEDERALLY SPONSORED RESEARCH OR DEVELOPMENT

This invention was made with government support under grant numbers AI102104, U54 AI057168, R41 AI113952, R44 AI125005, and R44 AI115759 awarded by the National Institutes of Health. The government has certain rights in the invention.

FIELD OF THE INVENTION

The invention relates to compounds or compositions for and methods of inhibiting, treating, or abrogating a molluscum contagiosum virus infection.

BACKGROUND OF THE INVENTION

Molluscum contagiosum (MC) is a skin disease caused by the poxvirus molluscum contagiosum virus (MCV). MC presents as skin lesions that can last from months to years before resolving. MC lesions occur in children, adults and immunosuppressed individuals and are restricted strictly to the skin. MCV is transmitted by direct skin-to-skin contact, sexual contact, auto-inoculation from scratching lesions and by indirect inoculation from contaminated fomites. The lesions can be painful following treatments intended to reduce spread. The lesions are also psychologically distressful, even more so when they result in scarring. MC occurs in 2-10% of the worldwide population and in the USA, it constitutes about 1% of all diagnosed skin disorders, and in children it approaches 5%. Significantly, in immunocompromised individuals, this infectious disease can be both severe and protracted. Between 5% and 18% of HIV patients have MC. Often, severe MC disease in AIDS patients begins to resolve while on highly active antiretroviral therapy (HAART). However, there have been documented cases of MC lesions developing soon after starting HAART, suggesting that immune reconstitution inflammatory syndrome (IRIS) might be playing a role in there-emergence of MCV.

The current treatments for MC usually employ physical therapy or chemical agents, which are not uniformly effective or safe, and often fail to completely eliminate lesions and may result in scaring. In addition, the broad-spectrum antiviral drug cidofovir, a dCMP analogue, has been used effectively as topical or intravenous medication for MC in immunocompromised patients, but with side effects including inflammation, erosion and pain for topical treatment and potential nephrotoxicity for systemic application. To date, there is not a single antiviral therapeutic that is licensed for the specific treatment of MC. The development of such an effective and safe treatment has been hampered mainly by the inability of MCV to propagate in culture.

Processivity factors (PFs) are attractive antiviral therapeutic targets. The function of PFs is to tether DNA polymerases (Pol) to the template to enable synthesis of extended strands. PFs are specific for theircognate DNA Pol and are absolutely essential for DNA synthesis. As a case in point, Kaposi's sarcoma herpes virus Pol (Pol-8) alone incorporates only three nucleotides, whereas in the presence of its PF, PF-8, it is able to incorporate many thousands of nucleotides. All DNA Pols from phage to human function with a single cognate PF. However, the prototypic poxvirus, vaccinia virus (VV) is somewhat unusual in that a heterodimer comprising the A20 and D4 viral proteins constitutes the functional PF. D4, which can also function as a uracil-DNA glycosylase repair enzyme, binds to its PF partner A20 but not to E9 Pol. A20 on the other hand, binds to both E9 and D4, suggesting that it serves, in part, as a bridge that indirectly connects D4 to E9. Therefore, effective therapeutics are needed for inhibiting, treating, or abrogating a molluscum contagiosum virus infection.

SUMMARY OF THE INVENTION

In one aspect, the present invention provides a compound of formula (IX)

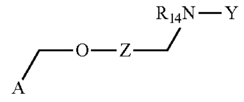

(IX)

wherein

A, Z, and Y is aryl or heteroaryl, each optionally substituted with $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, or heteroarylalkyl; or two adjacent $OR^a$ or $NR'''R''$ groups, together with the atoms to which they are attached, form a 5-7 membered heterocycloalkyl group;

$R^{14}$ is H, $C_1$-$C_3$ alkyl, $C(O)OR^a$, $C(O)R^b$, $C(O)NR'''R''$, $SOR^b$, or $SO_2R^b$;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl; and $R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 3-7 membered heterocycloalkyl group;

or a pharmaceutically acceptable salt thereof.

In another aspect, the present invention provides a composition comprising a compound of the invention described herein, for example, a compound of formula (I)-(XIV), or a pharmaceutically acceptable salt thereof, and at least one pharmaceutically acceptable carrier.

In yet another aspect, the present invention provides a method of inhibiting, treating, or abrogating a molluscum contagiosum virus infection in a subject in need thereof, the method comprising administering to said subject a therepeuatically effective amount of a compound of formula (IX), (IX)

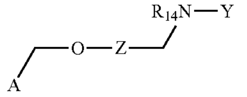

wherein

A, Z, and Y is aryl or heteroaryl, each optionally substituted with $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, to heteroaryl, $C_3$-$C_7$ cycloalkyl, 3-7 membered heterocycloalkyl, cycloalkylalkyl, heterocycloalkylalkyl, arylalkyl, or heteroarylalkyl; or two adjacent $OR^a$ or $NR'''R''$ groups, together with the atoms to which they are attached, form a 5-7 membered heterocycloalkyl group;

$R^{14}$ is H, $C_1$-$C_3$ alkyl, $C(O)OR^a$, $C(O)R^b$, $C(O)NR'''R''$, $SOR^b$, or $SO_2R^b$;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl; and $R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 3-7 membered heterocycloalkyl group;

or a pharmaceutically acceptable salt thereof.

In one aspect, the invention provides a compound of formula (I):

(I)

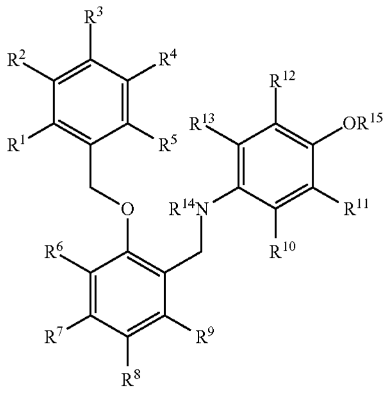

wherein $R^{14}$ is H, $C_1$-$C_3$ alkyl, $C(O)OR^a$, $C(O)R^b$, $C(O)NR'''R''$, $SOR^b$, or $SO_2R^b$;

$R^{15}$ is H, $C_1$-$C_5$ alkyl, $C(O)R^a$, $C(O)NR'''R''$;

$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;

$R'''$ and $R^a$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 3-7 membered heterocycloalkyl group;

wherein at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are not hydrogen;

or a pharmaceutically acceptable salt thereof.

In another aspect, the present invention provides a composition comprising a compound of formula (I), in which variables $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined anywhere herein, or a pharmaceutically acceptable salt thereof, and at least one pharmaceutically acceptable carrier.

In yet another aspect, the present invention provides a method of inhibiting, treating, or abrogating a molluscum contagiosum virus infection in a subject, the method comprising to administering to said subject a therapeutically effective amount of a compound of formula (I), (I)

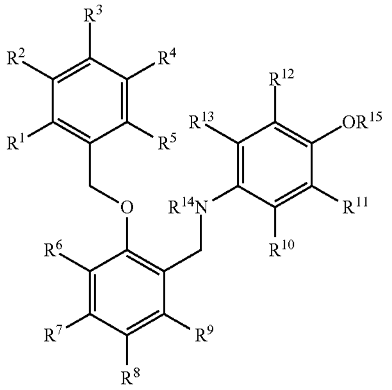

wherein $R^{14}$ is H, $C_1$-$C_3$ alkyl, $C(O)OR^a$, $C(O)R^b$, $C(O)NR'''R''$, $SOR^b$, or $SO_2R^b$;

$R^{15}$ is H, $C_1$-$C_5$ alkyl, $C(O)R^a$, $C(O)NR'''R''$;

$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;

$R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 3-7 membered heterocycloalkyl group;

or a pharmaceutically acceptable salt thereof.

The details of one or more embodiments of the invention are set forth in the accompanying description below. Other features, objects, and advantages of the invention will be apparent from the description and drawings, and from the claims.

BRIEF DESCRIPTION OF THE DRAWINGS

The invention will be better understood from a reading of the following detailed description taken in conjunction with the drawings in which like reference designators are used to designate like elements, and in which:

FIG. 5. Compound 10 binds mD4 and inhibits mD4-dependent processive DNA synthesis. (A) Molecular formula of compound 10 (Top). Thermal shift of 6His-mD4 in the presence of compound 10 (Bottom). Thermal shift (ΔTm) is the difference between DMSO mock treatment and compound 10. Note that the thermal shift of 6His-mD4 increases as the concentration of compound 10 is elevated from 10 μM (ΔTm: 2.2±SD 0.2° C.) to 40 μM (ΔTm: 3.3±SD 0.3° C.). The data were obtained from two independent experiments. (B) Inhibition of mD4-dependent processive DNA synthesis by compound 10. The Rapid Plate Assay was used to quantitate DNA synthesis conducted by purified 6His-mD4 and in vitro translated vA20 and vE9 in the presence of increasing concentrations of compound 10. $IC_{50}$ of compound 10=28 μM from two independent assays.

FIG. 9. (A) Alignment of mD4 and vD4. Identical amino acids are shaded. Missing amino acids are denoted by dashes. The C-terminal residues 167-180 and 191-206 of vD4 (underlined) are important for interacting with vA20. (B) Superimposition of mD4 predicted structure onto vD4 crystal structure. mD4 structure was generated by homology modeling using the SWISS-MODEL.

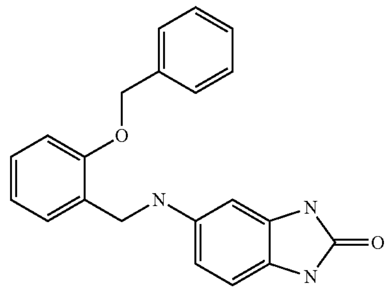 [SMILES: O=c1[nH]c2ccc(NCc3ccccc3OCc3ccccc3)cc2[nH]1]

to mD4 as determined by SPR. mD4 was immobilized onto a biosensor chip at 3500 RU, and compound 2 was injected at 0-250 μM in buffer with 1% DMSO. The binding affinity $K_D$ was determined from the plot of steady-state response (Req) against compound 2 concentrations and fitting to a 1:1 binding model.

Figure 11:
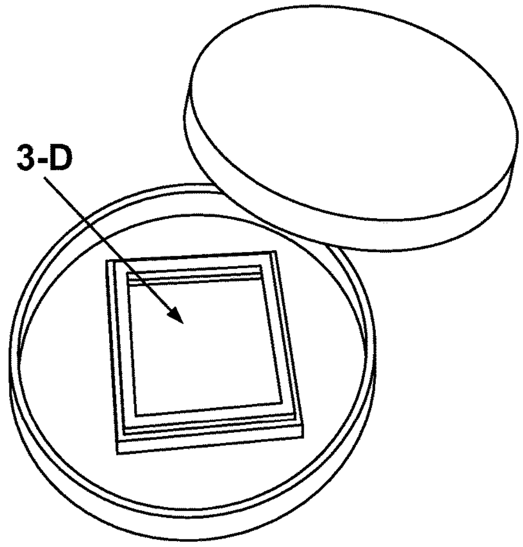

FIG. 11. 3-D human skin organ culture.

Figure 12:
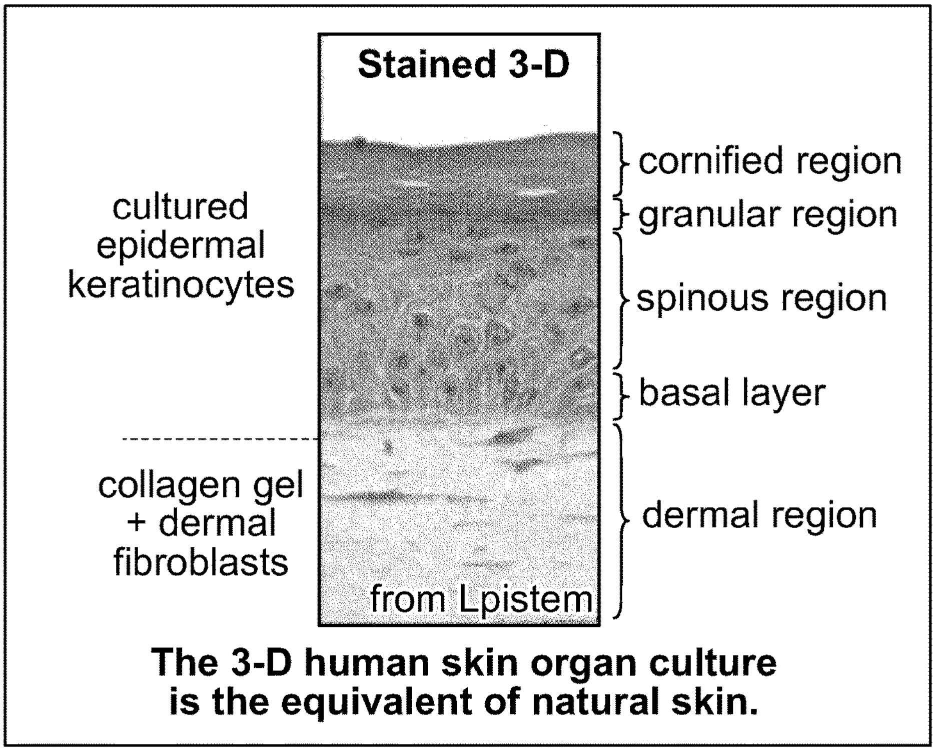

FIG. 12. Stained 3-D human skin organ culture.

Figure 13:
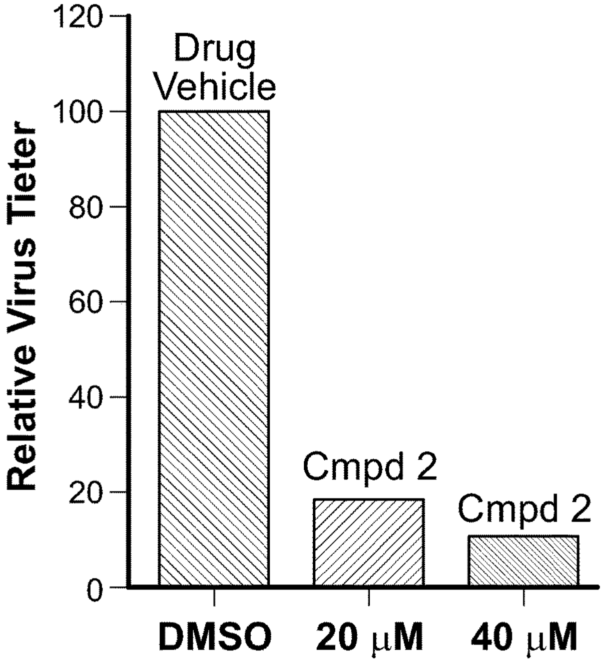

FIG. 13. Compound 2 blocks mD4-VV viral infection in the 3-D human skin organ culture.

Figure 14A:
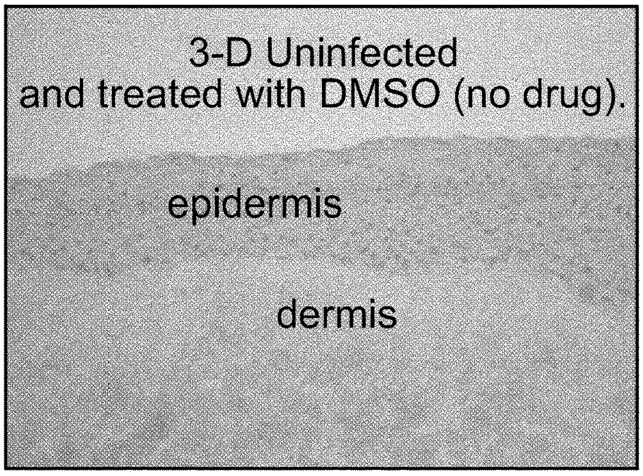
Figure 14B:
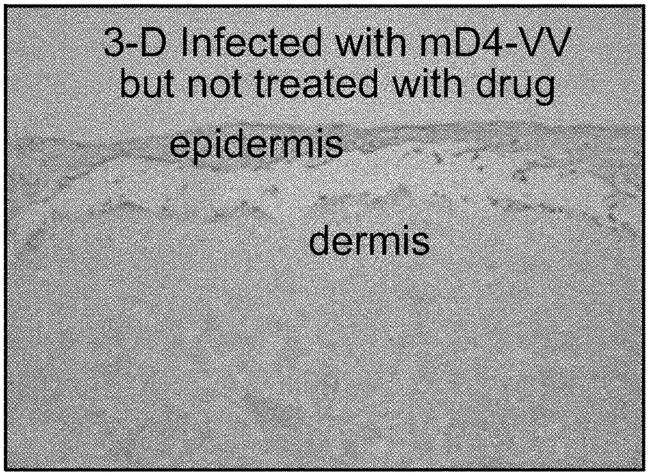
Figure 14C:
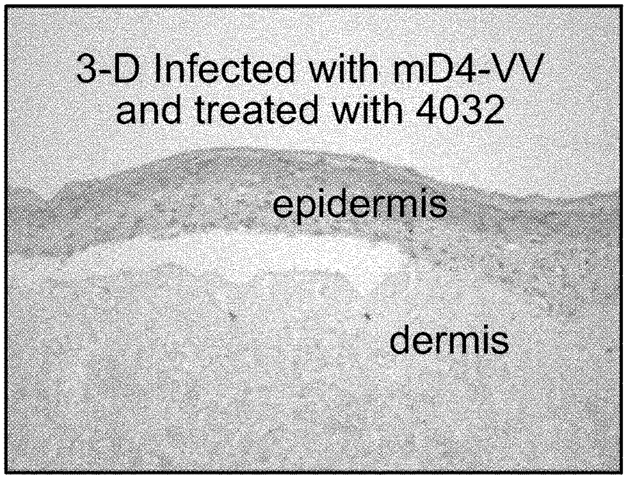

FIG. 14A-14C. Histological analysis shows protection of the 3-D human skin organ culture by compound 2. FIG.

14A: 3-D uninfected and treated with DMSO (no drug); FIG. 14B: 3-D infected with mD4-VV, but not treated with drug; and FIG. 14C: 3-D infected with mD4-VV and treated with compound 2.

Figure 15:
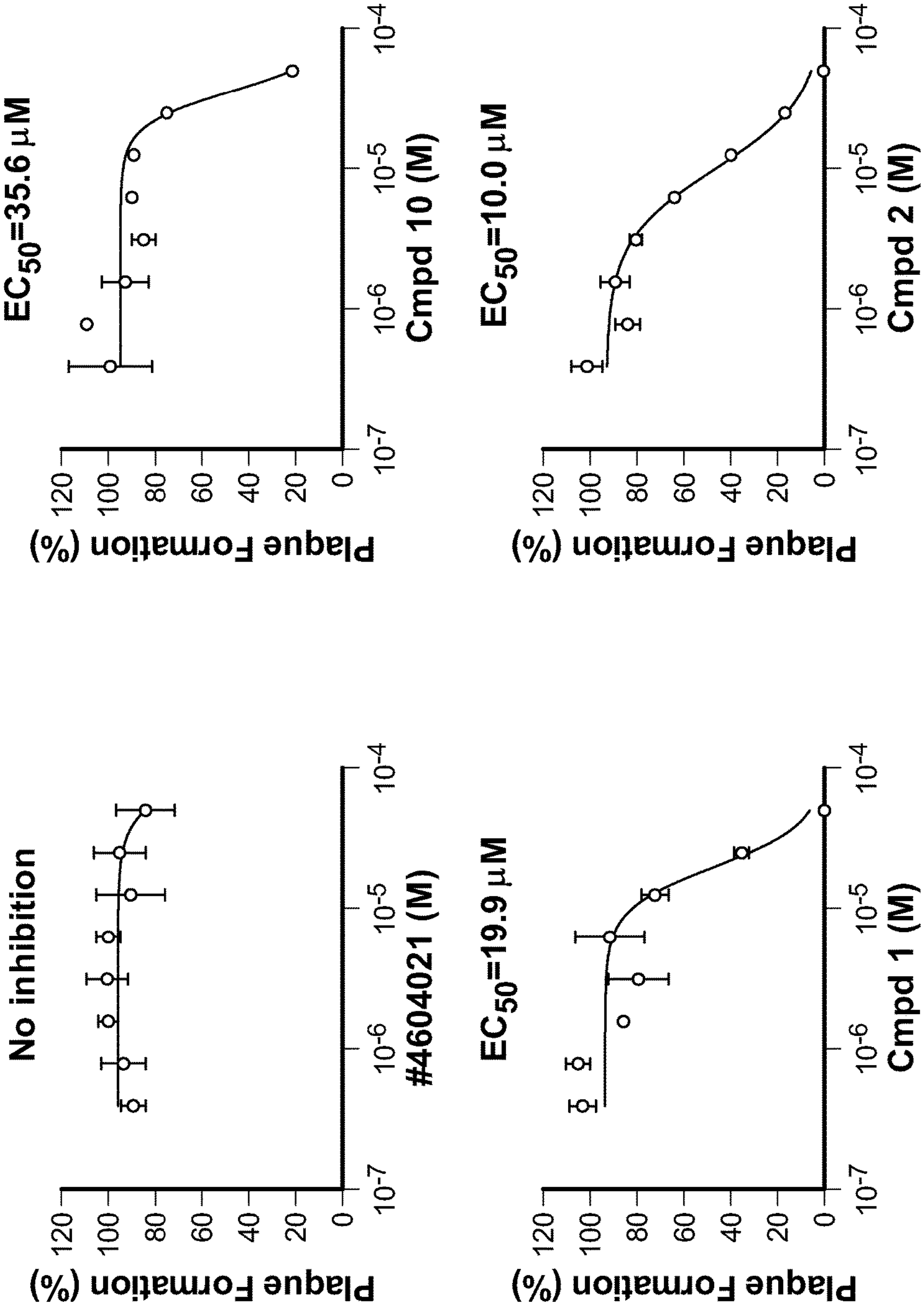
Figure 15:
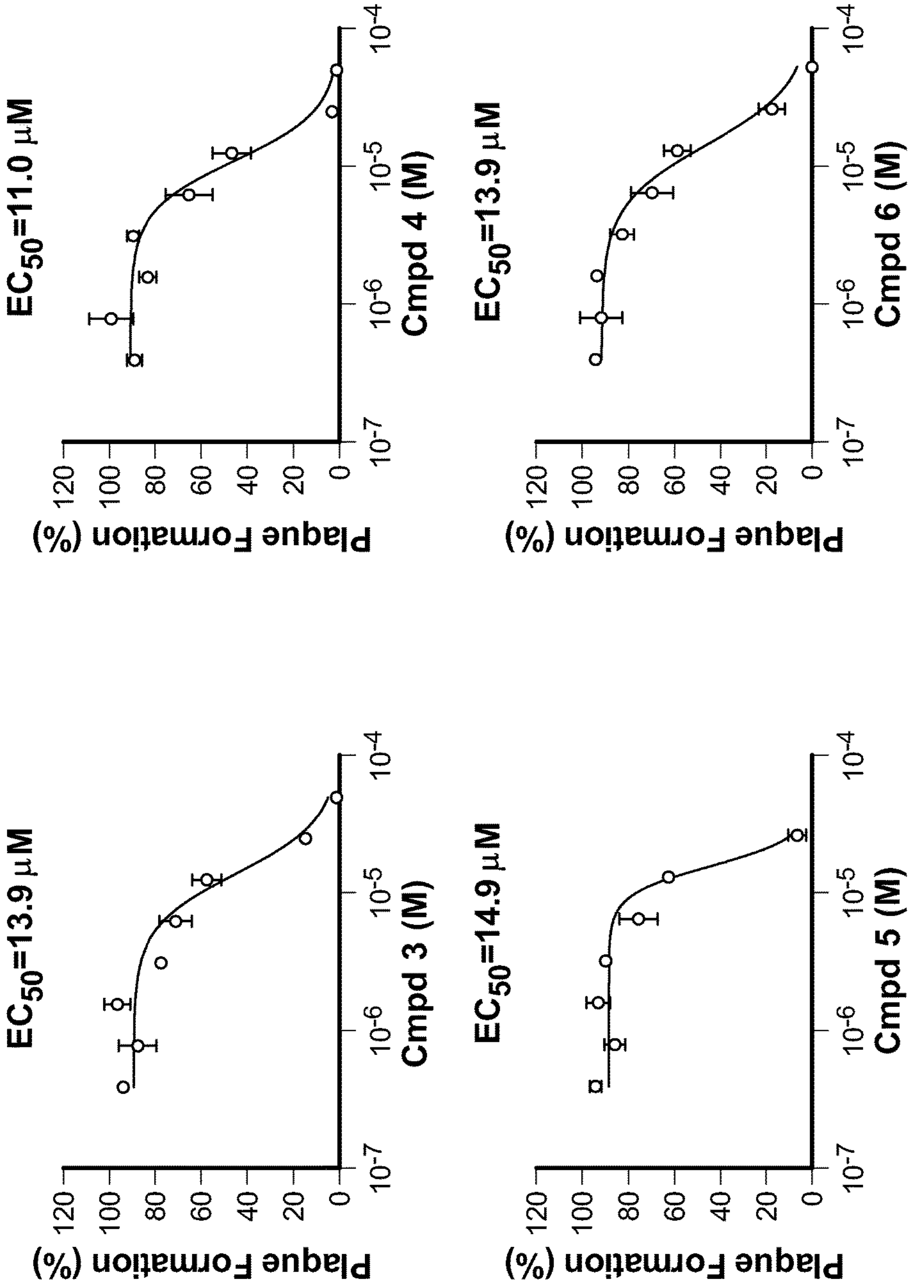
Figure 15:
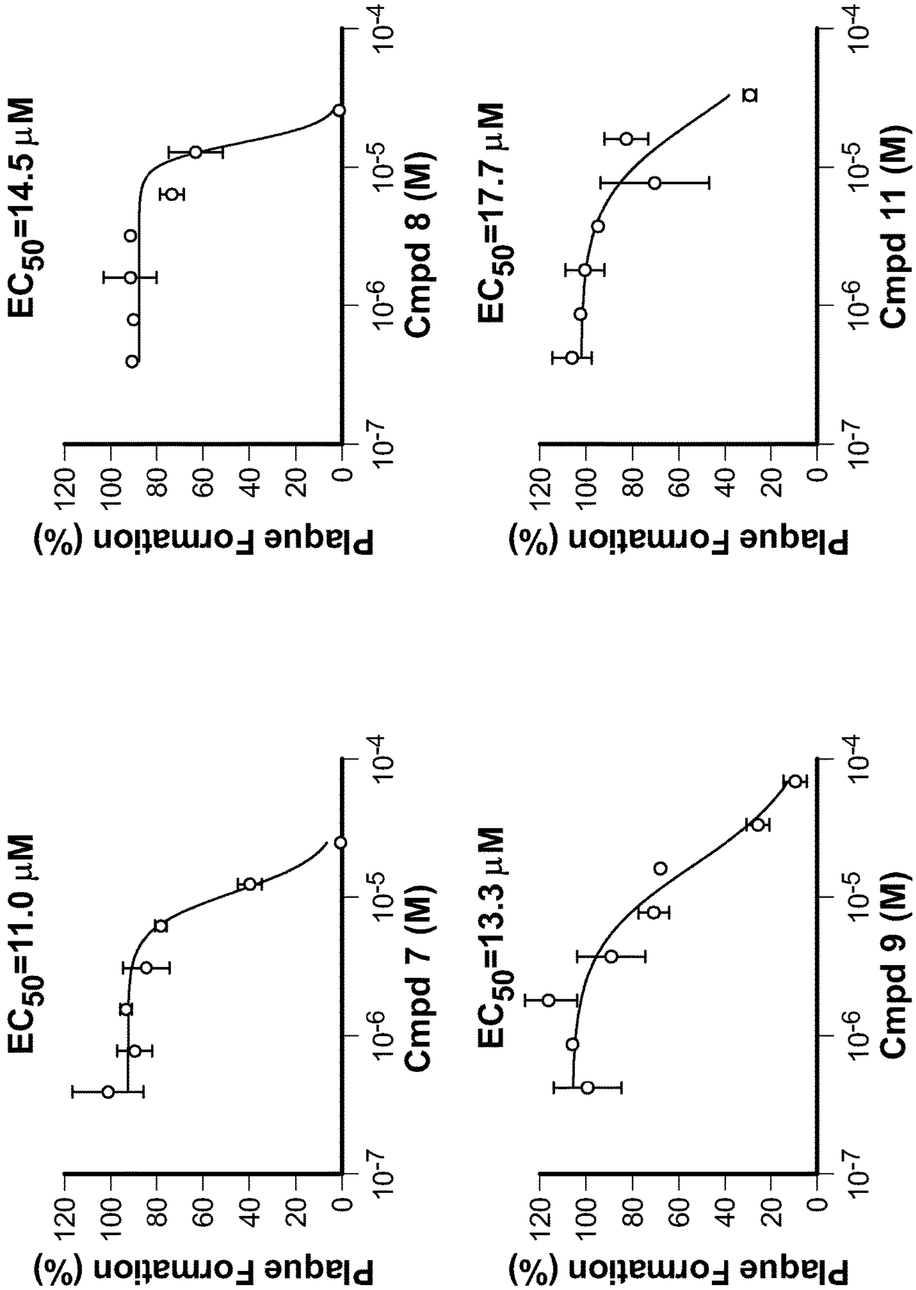
Figure 15:
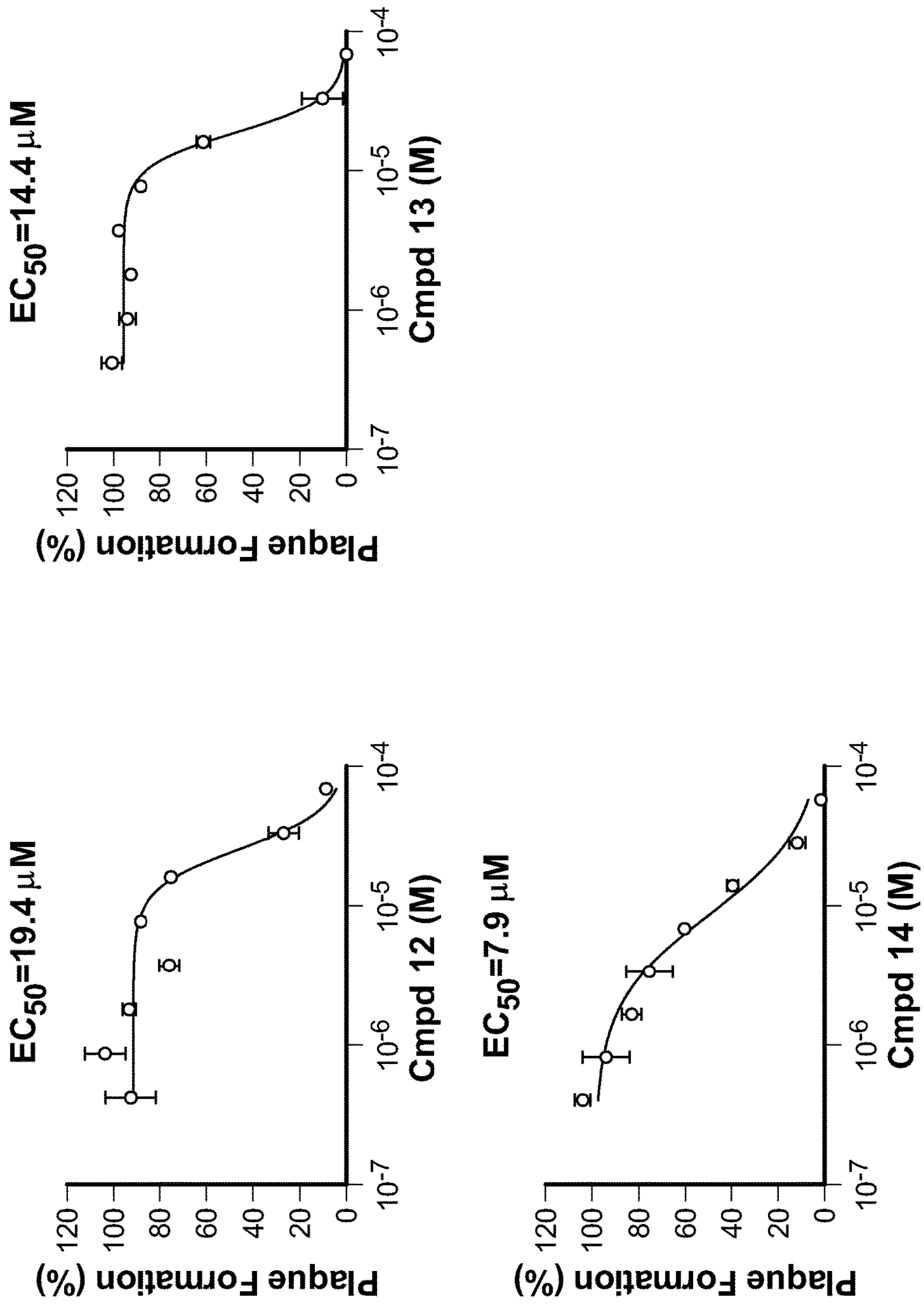

FIG. 15. mD4-VV plaque assay results for compounds 1-14.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The present invention is directed to, in some embodiments, to a compound of formula (IX)

(IX)

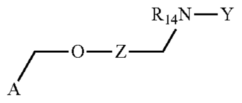

wherein

A, Z, and Y is aryl or heteroaryl, each optionally substituted with $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, or heteroarylalkyl; or two adjacent $OR^a$ or $NR'''R''$ groups, together with the atoms to which they are attached, form a 5-7 membered heterocycloalkyl group;

$R^{14}$ is H, $C_1$-$C_3$ alkyl, $C(O)OR^a$, $C(O)R^b$, $C(O)NR'''R''$, $SOR^b$, or $SO_2R^b$;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl; and $R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 3-7 membered heterocycloalkyl group.

or a pharmaceutically acceptable salt thereof.

In some embodiments, the compound is a compound of formula (X)

(X)

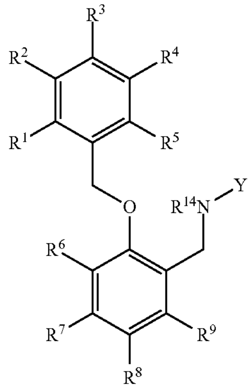

wherein

Y is heteroaryl; and $R^1$, $R^2$, $R^3$, $R^4$, $R^5$, $R^6$, $R^7$, $R^8$, and $R^9$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl; or two adjacent $OR^a$ or $NR'''R''$ groups, together with the atoms to which they are attached, form a 5-7 membered heterocycloalkyl group.

In some embodiments, $R^1$, $R^2$, $R^3$, $R^4$, $R^5$, $R^6$, $R^7$, $R^8$, and $R^9$ are each independently H, halo, cyano, nitro, $OR^a$, $C_1$-$C_6$ haloalkyl, $SO_2R^b$, $COR^b$, $COOR^a$, aryl, or heteroaryl. In some embodiments, $R^1$, $R^2$, $R^3$, $R^4$, $R^5$, $R^6$, $R^7$, $R^8$, and $R^9$ are each independently H or halo. In other embodiments, $R^1$, $R^2$, $R^3$, $R^4$, $R^5$, $R^6$, $R^7$, $R^8$, and $R^9$ are H.

In some embodiments, one of $R^1$, $R^2$, $R^3$, $R^4$, $R^5$, $R^6$, $R^7$, $R^8$, and $R^9$ is halo. In certain embodiments, one of $R^1$, $R^2$, $R^3$, $R^4$, and $R^5$ is halo and one of $R^6$, $R^7$, $R^8$, and $R^9$ is halo. In some embodiments, $R^1$, $R^2$, $R^3$, $R^4$, $R^5$, $R^6$, $R^7$, $R^8$, and $R^9$ are each independently H, halo, cyano, nitro, $CF_3$, or $SO_2NH_2$.

In some embodiments, Y is pyridine, pyrimidine, pyrazine, indole, indolizine, benzimidazole, 1,3-dihydrobenzimidazol-2-one, or indazole. In other embodiments, Y is pyridine, pyrimidine, pyrazine, indole, indolizine. In certain embodiments, Y is benzimidazole, 1,3-dihydrobenzimidazol-2-one, or indazole.

In some embodiments, the compound is a compound of formula (XI)

(XI)

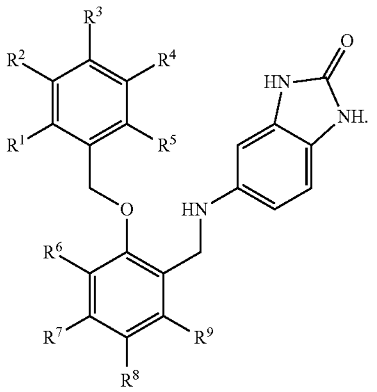

In some embodiments, the compound is a compound of formula (XII)

(XII)

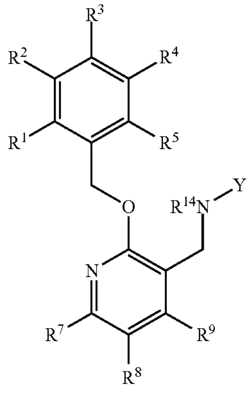

wherein

Y is heteroaryl; and $R^1$, $R^2$, $R^3$, $R^4$, $R^5$, $R^7$, $R^8$, and $R^9$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl; or two adjacent $OR^a$ or $NR'''R''$ groups, together with the atoms to which they are attached, form a 5-7 membered heterocycloalkyl group.

In some embodiments, $R^1$, $R^2$,$R^3$,$R^4$,$R^5$,$R^7$,$R^8$,and $R^9$ are each independently H, halo, cyano, nitro, $OR^a$, $C_1$-$C_6$ haloalkyl, $SO_2R^b$, $COR^b$, $COOR^a$, aryl, or heteroaryl. In other embodiments, $R^1$, $R^2$, $R^3$, $R^4$, $R^5$, $R^7$, $R^8$, and $R^9$ are each independently H or halo. In some embodiments, $R^1$, $R^2$, $R^3$, $R^4$, $R^5$, $R^7$, $R^8$, and $R^9$ are H. In other embodiments, one of $R^1$, $R^2$, $R^3$, $R^4$, $R^5$, $R^7$, $R^8$, and $R^9$ is halo.

In some embodiments, one of $R^1$, $R^2$, $R^3$, $R^4$, and $R^5$ is halo and one of $R^6$, $R^7$, $R^8$, and $R^9$ is halo. In other embodiments, $R^1$, $R^2$, $R^3$, $R^4$, $R^5$, $R^7$, $R^8$, and $R^9$ are each independently H, halo, cyano, nitro, $CF_3$, or $SO_2NH_2$.

In some embodiments, Y is pyridine, pyrimidine, pyrazine, indole, indolizine, benzimidazole, 1,3-dihydrobenzimidazol-2-one, or indazole. In other embodiments, Y is pyridine, pyrimidine, pyrazine, indole, indolizine. In certain embodiments, Y is benzimidazole, 1,3-dihydrobenzimidazol-2-one, or indazole.

In some embodiments, the compound of the present invention is a compound of formula (XIII)

(XIII)

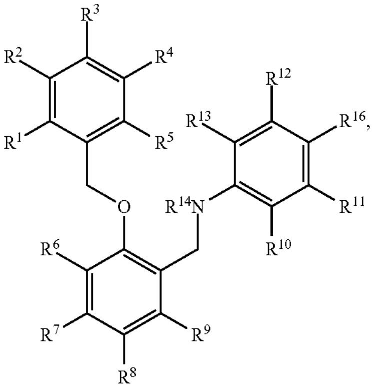

wherein $R^1$, $R^2$, $R^3$,$R^4$, $R^5$, $R^6$, $R^7$, $R^8$, $R^9$, $R^{10}$, $R^{11}$, $R^{12}$, $R^{13}$, and $R^{16}$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl, or two adjacent $OR^a$ or $NR'''R''$ groups, together with the atoms to which they are attached, form a 5-7 membered heterocycloalkyl group; and wherein when $R^{16}$ is $OR^a$, one of $R^1$, $R^2$, $R^3$, $R^4$, $R^5$, $R^6$, $R^7$, $R^8$, $R_9$, $R^{10}$, $R^{11}$, $R_{12}$, and $R^{13}$ is not H.

In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{16}$ are each independently H, halo, cyano, nitro, $OR^a$, $C_1$-$C_6$ haloalkyl, $SO_2R^b$, $COR^b$, $COOR^a$, aryl, or heteroaryl.

In some embodiments, one of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{16}$ is halo. In other embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{16}$ are each independently H, halo, cyano, nitro, OH, $CF_3$, or $SO_2NH_2$. In certain embodiments, when $R^{16}$ is $OR^a$, two of $R^1$, $R^2$, $R^3$, $R^4$, $R^5$, $R^6$, $R^7$, $R^8$, $R^9$, $R^{10}$, $R^{11}$, $R^{12}$, and $R^{13}$ are not H.

In some embodiments, the compound of the present invention is a compound of formula (I)

(I)

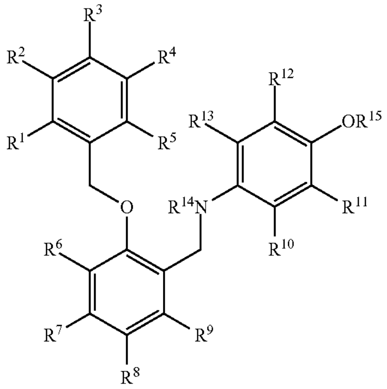

wherein $R^{15}$ is H, $C_1$-$C_5$ alkyl, $C(O)R^a$, $C(O)NR'''R''$;

$R^1$, $R^2$, $R^3$, $R^4$, $R^5$, $R^6$, R, $R^7$, $R^8$, $R^9$, $R^{10}$, $R^{11}$, $R^{12}$,and $R^{13}$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl; or two adjacent $OR^a$ or $NR'''R''$ groups, together with the atoms to which they are attached, form a 5-7 membered heterocycloalkyl group; and wherein at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are not H.

In some embodiments, at least two of $R^1$, $R^2$, $R^3$, $R^4$, $R^5$, $R^6$, $R^7$, $R^8$, $R^9$, $R^{10}$, $R^{13}$, $R^{14}$, and $R^{15}$ are not H.

In some embodiments, $R^{15}$ is H, $C_1$-$C_5$ alkyl.

In some embodiments, $R^{15}$ is H.

In some embodiments, $R^1$, $R^2$, $R^3$, $R^4$, $R^5$, $R^6$, $R^7$, $R^8$, $R^9$, $R^{10}$, $R^{11}$ and $R^{13}$ are each independently H, halo, cyano, nitro, $OR^a$, $C_1$-$C_6$ haloalkyl, $SO_2R^b$, $COR^b$, $COOR^a$, aryl, or heteroaryl. In other embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each independently H, halo, cyano, nitro, $CF_3$, or $SO_2NH_2$. In certain embodiments, one of $R^1$, $R^2$, $R^3$, $R^4$, $R^5$,$R^6$, $R^7$, $R^8$, $R^9$, $R^{10}$, $R^{11}$ , $R^{12}$, and $R^{13}$is halo.

In some embodiments, the compound of the present invention is a compound of formula (II)

(II)

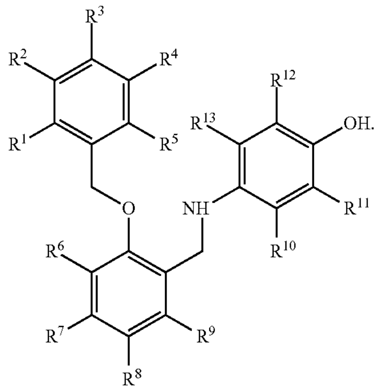

In some embodiments, the compound of the invention is a compound of formula (XIV)

(XIV))

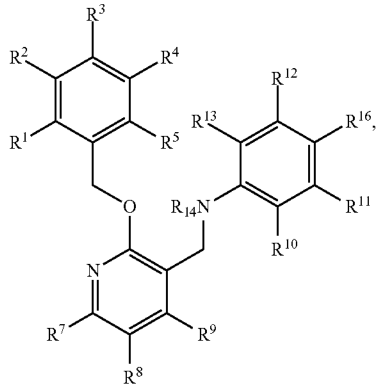

wherein $R^1$, $R^2$, $R^3$, $R^4$, $R^5$, $R^7$, $R^8$, $R^9$, $R^{10}$, $R^{11}$, $R^{12}$, $R^{13}$, and $R^{16}$ are each independently H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, or heteroarylalkyl; or two adjacent $OR^a$ or $NR'''R''$ groups, together with the atoms to which they are attached, form a 5-7 membered heterocycloalkyl group.

In some embodiments, $R^1$, $R^2$, $R^3$, $R^4$, $R^5$, $R^7$, $R^8$, $R^9$, $R^{10}$, $R^{11}$, $R^{12}$, $R^{13}$, and $R^{16}$ are each independently H, halo, cyano, nitro, $OR^a$, $C_1$-$C_6$ haloalkyl, $SO_2R^b$, $COR^b$, $COOR^a$, aryl, or heteroaryl. In some embodiments, $R^1$, $R^2$, $R^3$, $R^4$, $R^5$, $R^7$, $R^8$, $R^9$, $R^{10}$, $R^{11}$, $R^{12}$, $R^{13}$, and $R^{16}$ are each independently H or halo. In certain embodiments, $R^1$, $R^2$, $R^3$, $R^4$, $R^5$, $R^7$, $R^8$, $R^9$, $R^{10}$, $R^{11}$, $R^{12}$, $R^{13}$,and $R^{16}$ are H.

In some embodiments, one of $R^1$, $R^2$, $R^3$, $R^4$, $R^5$, $R^7$, $R^8$, $R^9$, $R^{10}$, $R^{11}$, $R^{12}$, $R^{13}$, and $R^{16}$ is halo. In other embodiments, $R^1$, $R^2$, $R^3$, $R^4$, $R^5$, $R^7$, $R^8$, $R^9$, $R^{10}$, $R^{11}$, $R^{12}$, $R^{13}$, and $R^{16}$ are each independently H, halo, cyano, nitro, $CF_3$, $SO_2NH_2$, aryl, or heteroaryl. In some embodiments, $R^1$, $R^2$, $R^3$, $R^4$, $R^5$, $R^7$, $R^8$, $R^9$, $R^{10}$, $R^{11}$, $R^{12}$, $R^{13}$, and $R^{16}$ are each independently H, halo, cyano, nitro, $CF_3$, or $SO_2NH_2$.

In some embodiments, $R^{14}$ is H or $C_1$-$C_3$ alkyl. In other embodiments, $R^{14}$ is H.

In some embodiments, the compound of the invention is:

5-[(2-benzyloxyphenyl)methylamino]-1,3-dihydrobenzimidazol-2-one,
5-[[2-[(4-chlorophenyl)methoxy]phenyl]methylamino]-1,3-dihydrobenzimidazol-2-one,
5-[[2-[(2-chlorophenyl)methoxy]phenyl]methylamino]-1,3-dihydrobenzimidazol-2-one,
5-[[2-[(4-fluorophenyl)methoxy]phenyl]methylamino]-1,3-dihydrobenzimidazol-2-one,
5-[(2-benzyloxy-5-bromo-phenyl)methylamino]-1,3-dihydrobenzimidazol-2-one,
5-[[5-chloro-2-[(2-fluorophenyl)methoxy]phenyl]methylamino]-1,3-dihydrobenzimidazol-2-one,
N-[2-benzyloxyphenyl)methyl]-1H-indazol-5-amine,
4-[[5-bromo-2-[(4-fluorophenyl)methoxy]phenyl]methylamino]phenol,
4-[(2-benzyloxy-5-chloro-phenyl)methylamino]benzenesulfonamide,
4-[[2-[(3-nitrophenyl)methoxy]phenyl]methylamino]phenol,
2-[[2-[(3-nitrophenyl)methoxy]phenyl]methylamino]phenol,
4-[(2-benzyloxyphenyl)methylamino]-3-fluoro-phenol, or
N-[(2-benzyloxyphenyl)methyl]-4-oxazol-5-yl-aniline.

This invention is directed to, in some embodiments, to a compound of formula (I)

(I)

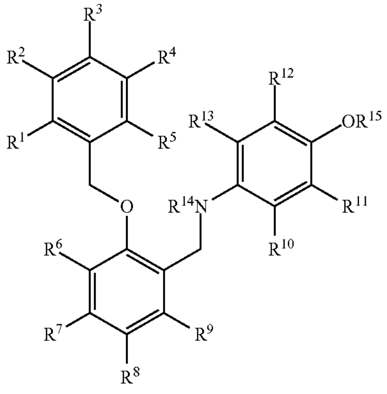

wherein $R^{14}$ is H, $C_1$-$C_3$ alkyl, $C(O)OR^a$, $C(O)R^b$, $C(O)NR'''R''$, $SOR^b$, or $SO_2R^b$;

$R^{15}$ is H, $C_1$-$C_5$ alkyl, $C(O)R^a$, $C(O)NR'''R''$;

$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_1$-$C_6$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;

$R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or R‴ and R″, together with the nitrogen atom to which they are attached, form a 3-7 membered heterocycloalkyl group;

wherein at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is not hydrogen.

In some embodiments, at least two of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are not hydrogen. In other embodiments, at least three of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are not hydrogen. In certain embodiments, more than three of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are not hydrogen.

In some embodiments, $R^{14}$ is H or $C_1$-$C_3$ alkyl.

In some embodiments, $R^{15}$ is H, $C_1$-$C_5$ alkyl.

In some embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each independently are H or $C_1$-$C_6$ alkyl. In some embodiments the alkyl is $CH_3$.

In some embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each independently selected from the group consisting of H, $C_1$-$C_6$ alkyl (e.g.,$CH_3$), halo, and $C_1$-$C_6$ alkoxy (e.g., $OCH_3$).

In some embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each independently selected from the group consisting of H, $CH_3$, and chloro.

In some embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ each independently are H or halo. In other embodiments, one of $R^1$, $R^2$, $R^3$, $R^4$, $R^5$, $R^6$, $R^7$, $R^8$, $R^9$, $R^{10}$, $R^{11}$, $R^{12}$, and $R^{13}$ is halo, for example, fluoro, chloro, or bromo. In other embodiments, two of $R^1$, $R^2$, $R^3$, $R^4$, $R^5$, $R^6$, $R^7$, $R^8$, $R^9$, $R^{10}$, $R^{11}$, $R^{12}$, and $R^{13}$ are halo, for example fluoro. In some embodiments, two of $R^1$, $R^2$, $R^3$, $R^4$, $R^5$, $R^6$, $R^7$, $R^8$, $R^9$, $R^{10}$, $R^{11}$, $R^{12}$, and $R^{13}$ are chloro. In some embodiments, three of $R^1$, $R^2$, $R^3$, $R^4$, $R^5$, $R^6$, $R^7$, $R^8$, $R^9$, $R^{10}$, $R^{11}$,$R^{12}$, and $R^{13}$ are halo. In certain embodiments, three of $R^1$, $R^2$, $R^3$, $R^4$, $R^5$, $R^6$, $R^7$, $R^8$, $R^9$, $R^{10}$, $R^{11}$, $R^{12}$, and $R^{13}$ are chloro. In other embodiments, more than three $R^1$, $R^2$, $R^3$, $R^4$, $R^5$, $R^6$, $R^7$, $R^8$, $R^9$, $R^{10}$, $R^{11}$, $R^{12}$, and $R^{13}$ are halo. In certain embodiments,more than three $R^1$, $R^2$, $R^3$, $R^4$, $R^5$, $R^6$, $R^7$, $R^8$, $R^9$, $R^{10}$, $R^{11}$, $R^{12}$, and $R^{13}$ are chloro.

In some embodiments, the compound of the invention can have formula (II)

(II)

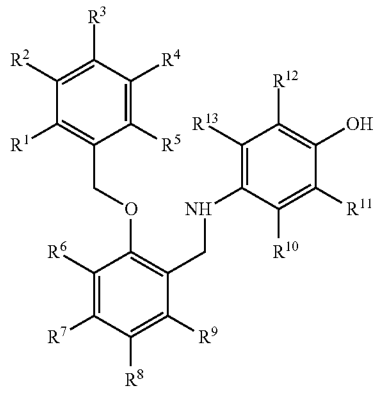

in which variables $R^1$, $R^2$, $R^3$, $R^4$, $R^5$, $R^6$, $R^7$ , $R^8$ ,$R^9$, $R^{10}$, $R^{11}$, $R^{12}$, and $R^{13}$ are as defined anywhere herein, or a pharmaceutically acceptable salt thereof.

In some embodiments, the compound of the invention can have formula (III)

(III)

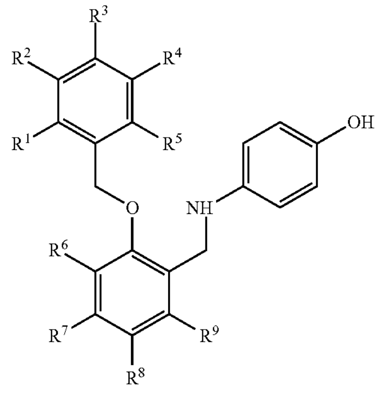

in which variables $R^1$, $R^2$, $R^3$, $R^4$, $R^5$, $R^6$, $R^7$, $R^8$, and $R^9$ are as defined anywhere herein, or a pharmaceutically acceptable salt thereof.

In some embodiments, the compound of the invention can have formula (IV)

(IV)

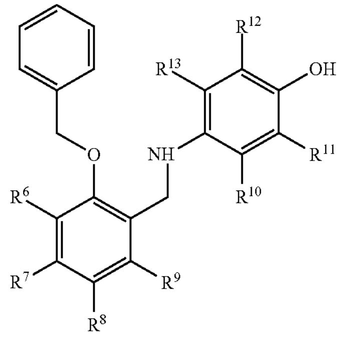

in which variables $R^6$, $R^7$, $R^8$, $R^9$, $R^{10}$, $R^{11}$, $R^{12}$, and $R^{13}$ are as defined anywhere herein, or a pharmaceutically acceptable salt thereof.

In some embodiments, the compound of the invention can have formula (V)

(V)

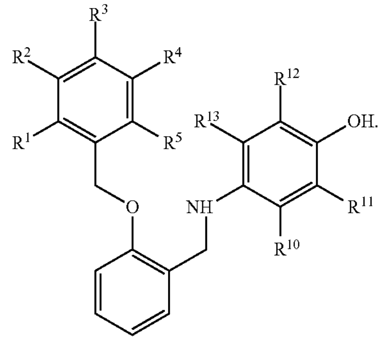

in which variables $R^1$, $R^2$, $R^3$, $R^4$, $R^5$,$R^{10}$, $R^{11}$, $R^{12}$, and $R^{13}$ are as defined anywhere herein, or a pharmaceutically acceptable salt thereof.

In some embodiments, the compound of the invention can have formula (VI)

(VI)

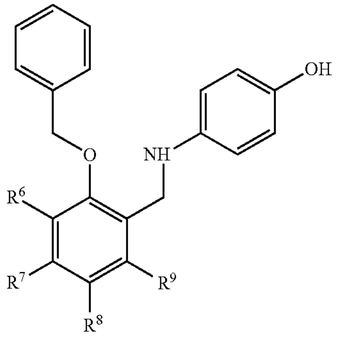

in which variables $R^6$, $R^7$, $R^8$, and $R^9$ are as defined anywhere herein, or a pharmaceutically acceptable salt thereof.

In some embodiments, the compound of the invention can have formula (VII)

(VII)

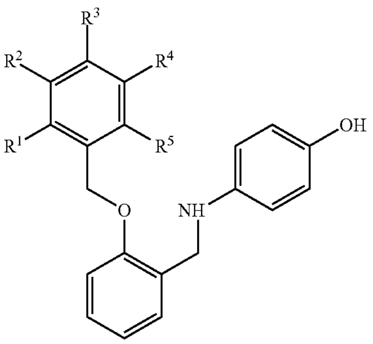

in which variables $R^1$, $R^2$, $R^3$, $R^4$, $R^5$, and $R^6$ are as defined anywhere herein, or a pharmaceutically acceptable salt thereof.

In some embodiments, the compound of the invention can have formula (VIII)

(VIII)

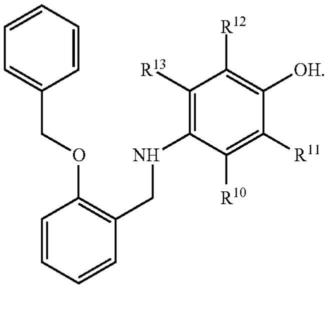

in which variables $R^{10}$, $R^{11}$, $R^{12}$, and $R^{13}$are as defined anywhere herein, or a pharmaceutically acceptable salt thereof.

At various places in the present specification, substituents of compounds of the invention are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

As used herein, the term "alkyl" refers to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

As used herein, "alkenyl" refers to an alkyl group having one or more double carbon-carbon bonds. Example alkenyl groups include ethenyl, propenyl, and the like.

As used herein, "alkynyl" refers to an alkyl group having one or more triple carbon-carbon bonds. Example alkynyl groups include ethynyl, propynyl, and the like.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. A cycloalkyl group having one or more fused aromatic rings is attached through either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, "cycloalkylalkyl" refers to an alkyl group substituted by a cycloalkyl group. Example cycloalkylalkyl groups include cyclopropylalkyl, cyclohexylalkyl, and the like.

As used herein, "heterocycloalkyl" refers to a non-aromatic heterocycle where one or more of the ring-forming atoms can be a heteroatom such as an O, N, or S atom. Heterocycloalkyl groups can include mono- or polycyclic (e.g., having 2, 3 or 4 fused rings) ring systems as well as spirocycles. Example heterocycloalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl can be moieties that have one or more aromatic rings fused (i.e., having a bond in common with) to the nonaromatic heterocyclic ring, for example phthalimidyl, naphthalimidyl, and benzo derivatives of heterocycles. A heterocycloalkyl group having one or more fused aromatic rings are attached though either the aromatic or non-aromatic portion. Also included in the definition of heterocycloalkyl can be moieties where one or more ring-forming atoms can be substituted by 1 or 2 oxo or sulfido groups. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "heterocycloalkylalkyl" refers to an alkyl group substituted by a heterocycloalkyl group. Example heterocycloalkylalkyl groups include morpholinoalkyl and piperazinylalkyl, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, an aryl group has from 6 to about 20 carbon atoms.

As used herein, "arylalkyl" refers to an alkyl group substituted by an aryl group. Example arylalkyl groups include benzyl and phenylethyl.

As used herein, a "heteroaryl" group refers to an aromatic heterocycle having at least one to heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, a "heteroarylalkyl" group refers to an alkyl group substituted by a heteroaryl group. An example of a heteroarylalkyl group is pyridylmethyl.

As used herein, "halo" or "halogen" includes fluoro, chloro, bromo, and iodo.

As used herein, "haloalkyl" refers to an alkyl group substituted by one or more halogen atoms. Examples of haloalkyl groups include $CF_3$ $C_2F_5$, $CHF_2$, $CCl_3$, $CHCl_2$, $C_2Cl_5$, and the like.

A compound of the present invention can be prepared simply from salicylaldehyde by alkylation of the phenol group with a suitable alkyl halide followed by reductive amination with 5-aminobenzimidazolone (Scheme 1).

Scheme 1 shows a synthetic method that was used in the preparation of the compounds of the present invention.

Scheme 1

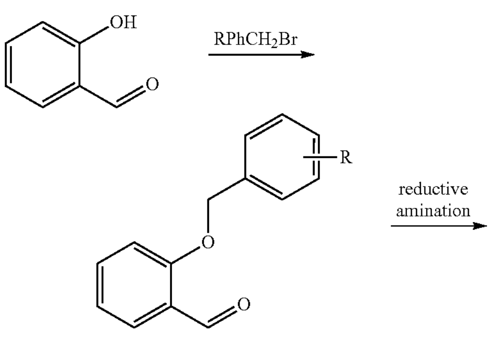

-continued

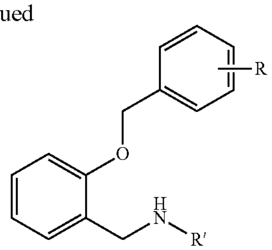

The compound of the present invention including variations of the aryl amine group can be obtained through reductive amination reactions of 2-benzyloxybenzaldehye, or other suitably functionalized benzaldehydes, with anilines Use of heterocyclic amines (aminopyridines, etc.) in place of anilines can lead to the compound of the present invention with a heterocyclic moiety, for example, exchanging anilines with benzylamines, phenethylamines, or other alkyl amines using the same synthetic process.

A compound of the present invention with a different central ring, represented by variable Z, such as pyridine-based compounds, can be prepared by starting from 2-chloro-3-formyipyridine, pyridine-based analogs of compound 2, where X═O or N, are accessible. The sequence of reaction with an amine (for X═N) or an alkoxide (for X═O) followed by reductive amination can provide easy access to a library of pyridine containing analogs (Scheme 2).

Scheme 2

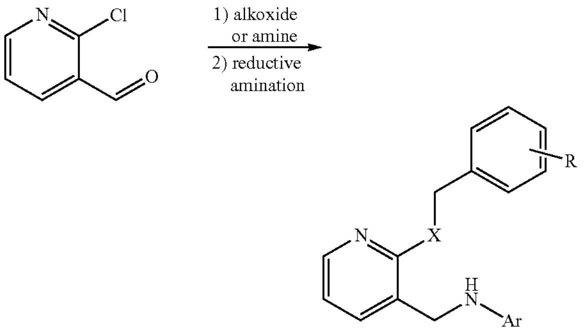

Alternately, when the central ring of a compound of formula (IX) is functionalized to introduce solubilizing groups, add hydrogen bond acceptor/donors, modulate lipophilicity, etc, brominated derivatives of salicylaldehyde can be used as starting materials in the described synthetic routes providing brominated intermediates. The bromine atom can then serve as a handle for further functionalization via standard palladium-catalyzed reactions, including arylation, amination, and aminocarbonylation, providing a compound of formula (IX) such as aromatic, heteroaromatic, amino, and amide derivatives of compound 2 enabling access to compounds with the targeted higher molecular weight.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention are synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts can be found in *Remington's Pharmaceutical Sciences*, $17^{th}$ ed., Mack Publishing Company, Easton, Pa., 1985, p. 1418 and *Journal of Pharmaceutical Science*, 66, 2 (1977), each of which is incorporated herein by reference in its entirety.

Examples of suitable inorganic acids include hydrochloric acid, sulphuric acid, phosphoric acid, or hydrobromic acid, while examples of suitable organic acids can include carboxylic acid, sulpho acid, or sulphonic acid, such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, maleic acid, salicylic acid, 3-aminosalicylic acid, ascorbic acid, embonic acid, nicotinic acid, isonicotinic acid, oxalic acid, gluconic acid, amino acids, methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid. Examples of suitable inorganic bases can include sodium hydroxide, potassium hydroxide and ammonia, while examples of suitable organic bases are amines, e.g., tertiary amines, such as trimethylamine, triethylamine, pyridine, N,N-dimethylaniline, quinoline, isoquinoline, α-picoline, β-picoline, γ-picoline, quinaldine, or pyrimidine.

As used herein, the phrase "pharmaceutically acceptable" is employed herein to refer to those compounds, materials, compositions, and/or dosage forms which can be, within the scope of sound medical judgment, suitable for use in contact with the tissues of human beings and animals without excessive toxicity, irritation, allergic response, or other problem or complication, commensurate with a reasonable benefit/risk ratio.

In some embodiments, the compound of the present invention, for example, a compound of formula (I), a compound of formula (II), a compound of formula (III), a compound of formula (IV), a compound of formula (V), a compound of formula (VI), a compound of formula (VII), or a compound of formula (VIII) can be linked to a lipid, or a derivative or analog thereof. The presence of a lipid, or a derivative or analog thereof, may promote disruption of biological membranes to facilitate intracellular delivery of the compound of the invention. The lipid includes, but is not limited to, (1) uncharged lipid components, for example, cholesterol, ceramide, diacylglycerol, acyl(poly ethers) or alkylpoly(ethers); (2) neutral phospholipids, for example, diacylphosphatidylcholines, sphingomyelins, and diacylphosphatidylethanolamines, (3) anionic lipids, for example, diacylphosphatidylserine, diacylphosphatidylglycerol, diacylphosphatidate, cardiolipin, diacylphosphatidylinositol, diacylglycerolhemisuccinate, diaclyglycerolhemigluratate, cholesterylhemisuccinate, cholesterylhemiglutarate, and the like; (4) polymer-conjugated lipids, for example, N-[methoxy-(poly(ethylene glycol)diacylphosphatidylethanolamine, poly(ethylene glycol)-diacylglycerol, poly(ethylene glycol)-ceramide; and (5) cationic lipids, for example, 1,2,-diacyl-3-trimethylammonium-propane (DOTAP), dimethyldioctadecylammonium bromide (DDAB), and 1,2-diacyl-sn-glycero-3-ethylphosphocholine.

The present invention further provides a method of inhibiting, treating, or abrogating a molluscum contagiosum virus infection in a subject in need thereof, the method comprising administering to said subject a therepeuatically effective amount of a compound of formula (IX), (IX)

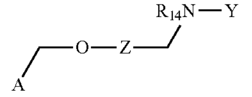

wherein

A, Z, and Y is aryl or heteroaryl, each optionally substituted with $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, or heteroarylalkyl; or two adjacent $OR^a$ or $NR'''R''$ groups, together with the atoms to which they are attached, form a 5-7 membered heterocycloalkyl group;

$R^{14}$ is H, $C_1$-$C_3$ alkyl, $C(O)OR^a$, $C(O)R^b$, $C(O)NR'''R''$, $SOR^b$, or $SO_2R^b$;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl; and $R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 3-7 membered heterocycloalkyl group.

or a pharmaceutically acceptable salt thereof.

In some embodiments, the compound for the method of the invention is a compound of formula (X)

(X)

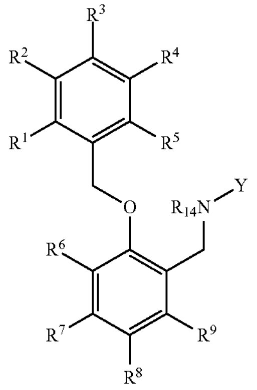

wherein

Y is heteroaryl; and $R^1$, $R^2$, $R^3$, $R^4$, $R^5$, $R^6$, $R^7$, $R^8$, and $R^9$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl; or two adjacent $OR^a$ or $NR'''R''$ groups, together with the atoms to which they are attached, form a 5-7 membered heterocycloalkyl group.

In some embodiments, $R^1$, $R^2$, $R^3$, $R^4$, $R^5$, $R^6$, $R^7$, $R^8$, and $R^9$ are each independently H, halo, cyano, nitro, $OR^a$, $C_1$-$C_6$ haloalkyl, $SO_2R^b$, $COR^b$, $COOR^a$, aryl, or heteroaryl. In other embodiments, $R^1$, $R^2$, $R^3$, $R^4$, $R^5$, $R^6$, $R^7$, $R^8$, and $R^9$ are each independently H or halo.

In some embodiments, $R^1$, $R^2$, $R^3$, $R^4$, $R^5$, $R^6$, $R^7$, $R^8$, and $R^9$ are H. In other embodiments, one of $R^1$, $R^2$, $R^3$, $R^4$, $R^5$, $R^6$, $R^7$, $R^8$, and $R^9$ is halo. In certain embodiments, one of $R^1$, $R^2$, $R^3$, $R^4$, and $R^5$ is halo and one of $R^6$, $R^7$, $R^8$, and $R^9$ is halo. In some embodiments, $R^1$, $R^2$, $R^3$, $R^4$, $R^5$, $R^6$, $R^7$, $R^8$, and $R^9$ are each independently H, halo, cyano, nitro, $CF_3$, or $SO_2NH_2$.

In some embodiments, Y is pyridine, pyrimidine, pyrazine, indole, indolizine, benzimidazole, 1,3-dihydrobenzimidazol-2-one, or indazole. In other embodiments, Y is pyridine, pyrimidine, pyrazine, indole, indolizine. In certain embodiments, Y is benzimidazole, 1,3-dihydrobenzimidazol-2-one, or indazole.

In some embodiments, the compound for the method of the invention is a compound of formula (XI)

(XI)

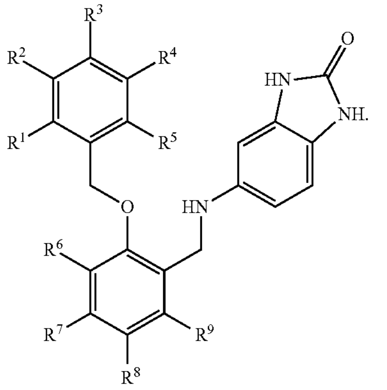

In some embodiments, the compound for the method of the invention is a compound of formula (XII)

(XII)

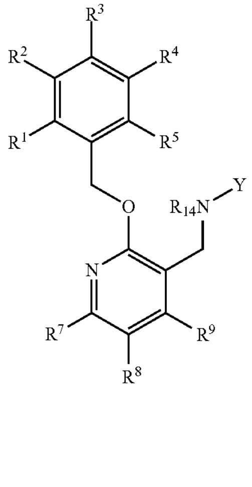

wherein

Y is heteroaryl; and $R^1$, $R^2$, $R^3$, $R^4$, $R^5$, $R^7$, $R^8$, and $R^9$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, to cycloalkylalkyl, heterocycloalkylalkyl, arylalkyl, and heteroarylalkyl; or two adjacent $OR^a$ or $NR'''R''$ groups, together with the atoms to which they are attached, form a 5-7 membered heterocycloalkyl group.

In some embodiments, $R^1$, $R^2$, $R^3$, $R^4$, $R^5$, $R^7$, $R^8$,and $R^9$ are each independently H, halo, cyano, nitro, $OR^a$, $C_1$-$C_6$ haloalkyl, $SO_2R^b$, $COR^b$, $COOR^a$, aryl, or heteroaryl. In certain embodiments, $R^1$, $R^2$, $R^3$, $R^4$, $R^5$, $R^7$, $R^8$, and $R^9$ are each independently H or halo. In other embodiments, $R^1$, $R^2$, $R^3$, $R^4$, $R^5$, $R^7$, $R^8$, and $R^9$ are H. In some embodiments, one of $R^1$, $R^2$, $R^3$, $R^4$, $R^5$, $R^7$, $R^8$, and $R^9$ is halo. In some embodiments, one of $R^1$, $R^2$, $R^3$, $R^4$, and $R^5$ is halo and one of $R^6$, $R^7$, $R^8$, and $R^9$ is halo. In some embodiments, $R^1$, $R^2$, $R^3$, $R^4$, $R^5$, $R^7$, $R^8$, and $R^9$ are each independently H, halo, cyano, nitro, $CF_3$, or $SO_2NH_2$.

In some embodiments, Y is pyridine, pyrimidine, pyrazine, indole, indolizine, benzimidazole, 1,3-dihydrobenzimidazol-2-one, or indazole. In other embodiments, Y is pyridine, pyrimidine, pyrazine, indole, indolizine. In certain embodiments, Y is benzimidazole, 1,3-dihydrobenzimidazol-2-one, or indazole.

In some embodiments, the compound for the method of the invention is a compound of formula (XIII)

(XIII)

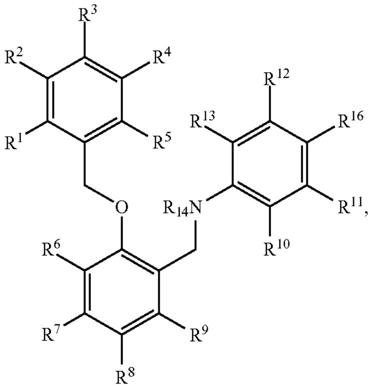

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{16}$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl; or two adjacent $OR^a$ or $NR'''R''$ groups, together with the atoms to which they are attached, form a 5-7 membered heterocycloalkyl group.

In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{16}$ are each independently H, halo, cyano, nitro, $OR^a$, $C_1$-$C_6$ haloalkyl, $SO_2R^b$, $COR^b$, $COOR^a$, aryl, or heteroaryl. In certain embodiments, one of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{16}$ is halo. In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{16}$ are each independently H, halo, cyano, nitro, OH, $CF_3$, or $SO_2NH_2$. In some embodiments, when $R^{16}$ is $OR^a$, two of $R^1$, $R^2$, $R^3$, $R^4$, $R^5$, $R^6$, $R^7$, $R^8$, $R^9$, $R^{10}$, $R^{11}$, $R^{12}$, and $R^{13}$ are not H.

In some embodiments, the compound for the method of the invention is a compound of formula (I)

(I)

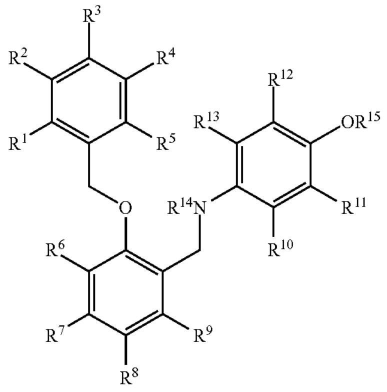

wherein $R^{15}$ is H, $C_1$-$C_5$ alkyl, C(O)$R^a$, C(O)NR$'''$R$''$;

$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from the group consisting of H, $C_1$-$C_6$ alkyl, halo, cyano, nitro, $C_1$-$C_6$ haloalkyl, $OR^a$, $SR^a$, NR$'''$R$''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl; or two adjacent $OR^a$ or NR$'''$R$''$ groups, together with the atoms to which they are attached, form a 5-7 membered heterocycloalkyl group.

In some embodiments, at least two of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are not H.

In some embodiments, $R^{15}$ is H, $C_1$-$C_5$ alkyl.

In some embodiments, $R^{15}$ is H.

In some embodiments, $R^1$, $R^2$, $R^3$, $R^5$, $R^6$, $R^7$, $R^8$, $R^9$, $R^{10}$, $R^{11}$, $R^{12}$, and $R^{13}$ are each independently H, halo, cyano, nitro, $OR^a$, $C_1$-$C_6$ haloalkyl, $SO_2R^b$, $COR^b$, $COOR^a$, aryl, or heteroaryl. In other embodiments, $R^1$, $R^2$, $R^3$, $R^4$, $R^5$, $R^6$, $R^7$, $R^8$, $R^{11}$ and $R^{13}$ are each independently H, halo, cyano, nitro, $CF_3$, or $SO_2NH_2$. In some embodiments, one of $R^1$, $R^2$, $R^3$, $R^4$, $R^5$, $R^6$, $R^7$, $R^8$, $R^9$, $R^{10}$, $R^{11}$, $R^{12}$, and $R^{13}$ is halo.

In some embodiments, the compound for the method of the invention is a compound of formula (II)

(II)

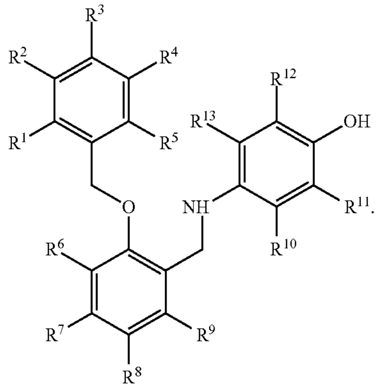

In some embodiments, the compound for the method of the invention is a compound of formula (XIV)

(XIV)

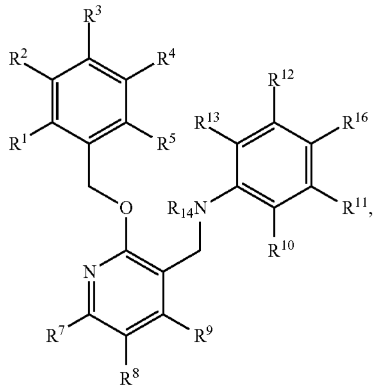

wherein $R^1$, $R^2$, $R^3$, $R^4$, $R^5$, $R^7$, $R^8$, $R^9$, $R^{10}$, $R^{12}$, $R^{13}$, and $R^{16}$ are each independently H, $C_1$-$C_6$ alkyl, halo, cyano, nitro, $C_1$-$C_6$ haloalkyl, $OR^a$, $SR^a$, NR$'''$R$''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, to heterocycloalkylalkyl, arylalkyl, or heteroarylalkyl; or two adjacent $OR^a$ or NR$'''$R$''$ groups, together with the atoms to which they are attached, form a 5-7 membered heterocycloalkyl group.

In some embodiments, $R^1$, $R^2$, $R^3$, $R^4$, $R^5$, $R^7$, $R^8$, $R^9$, $R^{10}$, $R^{11}$, $R^{12}$, $R^{13}$, and $R^{16}$ are each independently H, halo, cyano, nitro, $OR^a$, $C_1$-$C_6$ haloalkyl, $SO_2R^b$, $COR^b$, $COOR^a$, aryl, or heteroaryl. In some embodiments, $R^1$, $R^2$, $R^3$, $R^4$, $R^5$, $R^7$, $R^8$, $R^9$, $R^{10}$, $R^{11}$, $R^{12}$, $R^{13}$, and $R^{16}$ are each independently H or halo. In certain embodiments, $R^1$, $R^2$, $R^3$, $R^4$, $R^5$, $R^7$, $R^8$, $R^9$ , $R^{10}$, $R^{11}$, $R^{12}$, $R^{13}$, and $R^{16}$ are H. In other embodiments, one of $R^1$, $R^2$, $R^3$, $R^4$, $R^5$, $R^7$, $R^8$, $R^9$, $R^{10}$ , $R^{11}$, $R^{12}$, $R^{13}$, and $R^{16}$ is halo. In some embodiments, $R^1$, $R^2$, $R^3$, $R^4$, $R^5$, $R^7$, $R^8$, $R^9$, $R^{10}$, $R^{11}$, $R^{12}$, $R^{13}$, and $R^{16}$ are each independently H, halo, cyano, nitro, $CF_3$, $SO_2NH_2$, aryl, or heteroaryl. In some embodiments, $R^1$, $R^2$, $R^3$, $R^4$, $R^5$, $R^7$, $R^8$, $R^9$, $R^{10}$, $R^{11}$, $R^{12}$, $R^{13}$, and $R^{16}$ are each independently H, halo, cyano, nitro, $CF_3$, or $SO_2NH_2$.

In some embodiments, $R^{14}$ is H or $C_1$-$C_3$ alkyl. In some embodiments, $R^{14}$ is H.

In some embodiments, the compond for the method of the invention is:

5-[(2-benzyloxyphenyl)methylamino]-1,3-dihydrobenzimidazol-2-one,

5-[[2-[(4-chlorophenyl)methoxy]phenyl]methylamino]-1,3-dihydrobenzimidazol-2-one, 5-[[2-[(2-chlorophenyl)methoxy]phenyl]methylamino]-1,3-dihydrobenzimidazol-2-one, 5-[[2-[(4-fluorophenyl)methoxy]phenyl]methylamino]-1,3-dihydrobenzimidazol-2-one, 5-[(2-benzyloxy-5-bromo-phenyl)methylamino]-1,3-dihydrobenzimidazol-2-one, 5-[[5-chloro-2-[(2-fluoropheny)methoxy]phenyl]methylamino]-1,3-dihydrobenzimidazol-2-one, N-[(2-benzyloxyphenyl)methyl]-1H-indazol-5-amine, 4-[[5-bromo-2-[(4-fluoropheny)methoxy]phenyl]methylamino]phenol, 4-[(2-benzyloxy-5-chloro-pheny)methylamino]benzenesulfonamide, 4-[[2-[(3-nitropheny)methoxy]phenyl]methylamino]phenol, 2-[[2-[(3-nitropheny)methoxy]phenyl]methylamino]phenol, 4-[(2-benzyloxypheny)methylamino]phenol, 4-[(2-benzyloxypheny)methylamino]-3-fluoro-phenol, or N-[2-benzyloxyphenyl)methyl]-4-oxazol-5-yl-aniline In some embodiments, the compound for the method of the invention reduces, inhibits, or abrogates interaction of a DNA polymerase with a processivity factor.

The present invention provides a method of inhibiting, treating, or abrogating a poxvirus infection in a subject in need thereof, the method comprising administering to said subject a therapeutically effective amount of a compound of formula (I), (I)

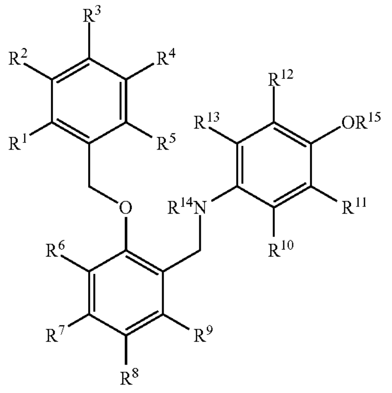

wherein $R^{14}$ is H, $C_1$-$C_3$ alkyl, $C(O)OR^a$, $C(O)^b$, $C(O)NR'''R''$, $SOR^b$, or $SO_2R^b$;

$R^{15}$ is H, $C_1$-$C_5$ alkyl, $C(O)R^a$, $C(O)NR'''R^a$;

$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;

$R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 3-7 membered heterocycloalkyl group.

In some embodiments, the compound for the method of the invention can have formula (II)

(II)

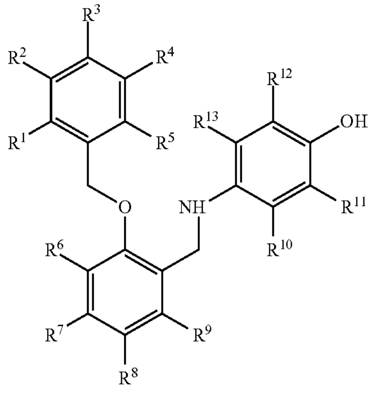

in which variables $R^1$, $R^2$, $R^3$, $R^4$, $R^5$, $R^6$, $R^7$, $R^8$ , $R^9$, $R^{10}$ , $R^{11}$, $R^{12}$, and $R^{13}$ are as defined to anywhere herein, or a pharmaceutically acceptable salt thereof.

In some embodiments, the compound for the method of the invention can have formula (III)

(III)

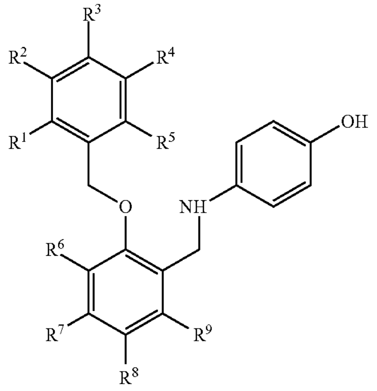

in which variables $R^1$, $R^2$, $R^3$, $R^4$, $R^5$, $R^6$, $R^7$, $R^8$, and $R^9$ are as defined anywhere herein, or a pharmaceutically acceptable salt thereof.

In some embodiments, the compound for the method of the invention can have formula (IV)

(IV)

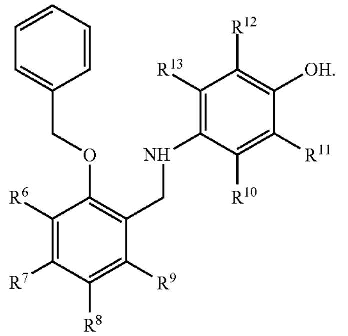

in which variables $R^6$, $R^7$, $R^8$, $R^9$, $R^{10}$, $R^{11}$, $R^{12}$, and $R^{13}$ are as defined anywhere herein, or a pharmaceutically acceptable salt thereof.

In some embodiments, the compound for the method of the invention can have formula (V)

(V)

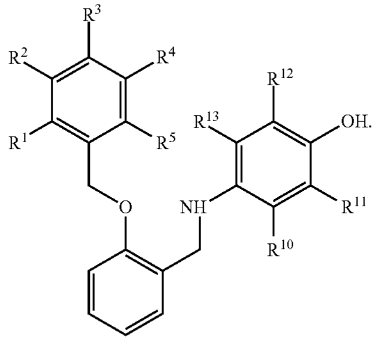

in which variables $R^1$, $R^2$, $R^3$, $R^4$, $R^5$, $R^{10}$, $R^{11}$, $R^{12}$, and $R^{13}$ are as defined anywhere herein, or a pharmaceutically acceptable salt thereof.

In some embodiments, the compound for the method of the invention can have formula (VI)

(VI)

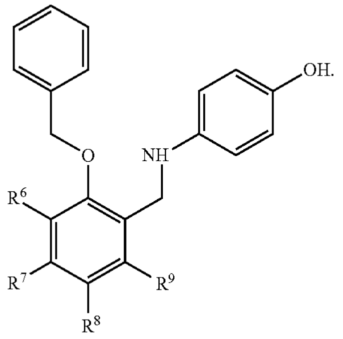

in which variables $R^6$, $R^7$, $R^8$, and $R^9$ are as defined anywhere herein, or a pharmaceutically acceptable salt thereof.

In some embodiments, the compound for the method of the invention can have formula (VII)

(VII)

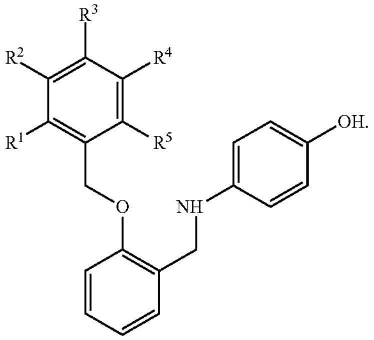

in which variables $R^1$, $R^2$, $R^3$, $R^4$, $R^5$, and $R^6$ are as defined anywhere herein, or a pharmaceutically acceptable salt thereof.

In some embodiments, the compound for the method of the invention can have formula (VIII)

(VIII)

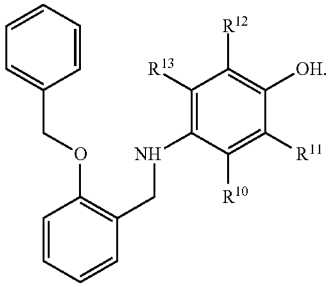

in which variables $R^{10}$, $R^{11}$, $R^{12}$, and $R^{13}$are as defined anywhere herein, or a pharmaceutically acceptable salt thereof.

In some embodiments, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ is not hydrogen. In some embodiments, at least two of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are not hydrogen. In other embodiments, at least three of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are not hydrogen. In certain embodiments, more than three of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are not hydrogen.

In some embodiments, $R^{14}$ is H or $C_1$-$C_3$ alkyl.

In some embodiments, $R^{15}$ is H, $C_1$-$C_5$ alkyl.

In some embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each independently are H or $C_1$-$C_6$ alkyl. In some embodiments the alkyl is $CH_3$.

In some embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each independently selected from the group consisting of H, $C_1$-$C_6$ alkyl (e.g. ,$CH_3$), halo, and $C_1$-$C_6$ alkoxy (e.g., $OCH_3$).

In some embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ are each independently selected from the group consisting of H, $CH_3$, and chloro.

In some embodiments, $R^1$, $R^2$, $R^3$, $R^4$, $R^5$, $R^6$, $R^7$, $R^8$, $R^9$, $R^{10}$, $R^{11}$, $R^{12}$, and $R^{13}$ each independently are H or halo. In other embodiments, one of $R^1$, $R^2$, $R^3$, $R^4$, $R^5$, $R^6$, $R^7$, $R^8$, $R^9$, $R^{10}$, $R^{11}$, $R^{12}$, and $R^{13}$ is halo, for example, fluoro, chloro, or bromo. In other embodiments, two of $R^1$, $R^2$, $R^3$, $R^4$, $R^5$, $R^6$, $R^7$, $R^8$, $R^9$, $R^{10}$, $R^{11}$, $R^{12}$, and $R^{13}$ are halo, for example fluoro. In some embodiments, two of $R^1$, $R^2$, $R^3$, $R^4$, $R^5$, $R^6$, $R^7$, $R^8$, $R^9$,$R^{10}$,$R^{11}$, $R^{12}$, and $R^{13}$are chloro. In some embodiments, three of $R^1$, $R^2$, $R^3$, $R^4$, $R^5$, $R^6$, $R^7$, $R^8$, $R^9$, $R^{10}$, $R^{11}$, $R^{12}$, and $R^{13}$are halo. In certain embodiments, three of $R^1$, $R^2$, $R^3$, $R^4$, $R^5$, $R^6$, $R^7$, $R^8$, $R^9$, $R^{10}$, $R^{11}$, $R^{12}$, and $R^{13}$ are chloro. In other embodiments, more than three $R^1$, $R^2$, $R^3$, $R^4$, $R^5$, $R^6$, $R^7$, $R^8$, $R^9$, $R^{10}$, $R^{11}$, $R^{12}$, and $R^{13}$ are halo. In certain embodiments,more than three $R^1$, $R^2$, $R^3$, $R^4$, $R^5$, $R^6$, $R^7$, $R^8$, $R^9$, $R^{10}$, $R^{11}$, $R^{12}$, and $R^{13}$ are chloro.

In some embodiments, the compound for the method of the invention is (4-({[2-(benzyloxy)phenyl]methyl}amino) phenol) (compound 10) shown below.

compound 10

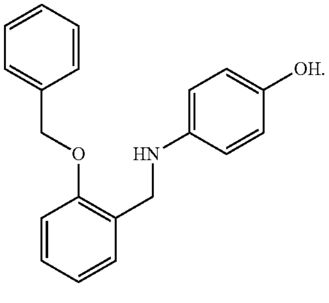

In some embodiments, the step of inhibiting a poxvirus infection in a subject can include the step of inhibiting DNA synthesis of said molluscum contagiosum virus.

In some embodiments, the DNA polymerase is an E9 DNA polymerase.

In some embodiments, the compound can reduce, inhibit, or abrogate interaction of said DNA polymerase with a processivity factor. In some embodiments, the processivity factor is an A20 or D4R processivity factor.

In some embodiments, the subject is a human.

The method of inhibiting, treating, or abrogating a poxvirus infection in a subject comprises the step of administering to said subject an effective amount compound of the present invention. The term "an effective amount" or "a therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, methods of inhibiting replication of a molluscum contagiosum virus comprise methods of inhibiting the DNA thereof. In certain embodiments, inhibiting the DNA replication is achieved by inhibiting activity of a DNA polymerase protein. In certain embodiments, inhibiting a DNA polymerase protein activity comprises reducing the processivity of a DNA polymerase.

In certain embodiments, a compound as described herein is solubilized in a buffer compatible with the media comprising cells or a tissue culture. In another embodiment, a compound as described herein is solubilized in the media comprising cells or a tissue culture. In certain embodiments, a compound as described herein is suspended or otherwise emulsified by methods known to one skilled in the art.

In certain embodiments, the present invention provides methods of inhibiting, a molluscum contagiosum virus infection in an animal and/or subject comprising administering to an animal and/or subject a compound of the present invention In some embodiments, the compound of the present invention utilized in methods as described herein can have an $IC_{50}$ for a molluscum contagiosum virus of about 30 nM. In some embodiments, the $IC_{50}$ are about 100 nM. In other embodiments, the $IC_{50}$ are about 200 nM.

In some embodiments, the compound of the present invention utilized in methods as described herein can have an $IC_{50}$ for a molluscum contagiosum virus of about 10,000 nM or less. In some embodiments, the compound of the invention can have an $IC_{50}$ of about 5,000 nM or less. In some embodiments, the compound of the invention can have an $IC_{50}$ of about 1,000 nM or less. In some embodiments, the compound of the invention can have an $IC_{50}$ of about 750 nM or less. In some embodiments, the compound of the invention can have an $IC_{50}$ of about 500 nM or less. In some embodiments, the compound of the invention can have an $IC_{50}$ of about 250 nM or less. In some embodiments, the compound of the invention can have an $IC_{50}$ of about 200 nM or less. In other embodiments, the compound of the invention can have an $IC_{50}$ of about 175 nM or less. In other embodiments, the compound of the invention can have an $IC_{50}$ of 150 nM or less. In some embodiments, the compound of the invention can have an $IC_{50}$ of about 125 nM or less. In some embodiments, the compound of the invention can have an $IC_{50}$ of about 100 nM or less. In certain embodiments, the compound of the invention can have an $IC_{50}$ of about 75 nM or less. In other embodiments, the compound of the invention can have an $IC_{50}$ of about 50 nM or less. In certain embodiments, the compound of the invention can have an $IC_{50}$ of about 30 nM or less. In other embodiments, the compound of the invention can have an $IC_{50}$ of about 20 nM or less.

In some embodiments, the compound of the present invention utilized in methods as described herein can have an $IC_{50}$ for a molluscum contagiosum virus of about 40 nM. In some embodiments, the compound of the present invention utilized in methods as described herein can have an $IC_{50}$ for a poxvirus of about 50 nM. In some embodiments, the compound of the present invention utilized in methods as described herein can have an $IC_{50}$ for a poxvirus of about 200 nM. In some embodiments, the compound of the present invention utilized in methods as described herein can have an $IC_{50}$ for a poxvirus of about 250 nM.

In some embodiments, the compound of the present invention utilized in methods as described herein can have an $IC_{50}$ for a molluscum contagiosum virus of from about 100,000 nM or less. In some embodiments, the compound of the invention can have an $IC_{50}$ of about 75,000 nM or less. In some embodiments, the compound of the invention can have an antiviral $IC_{50}$ of about 50,000 nM or less. In some embodiments, the compound of the invention can have an $IC_{50}$ of about 25,000 nM or less. In some embodiments, the compound of the invention can have an $IC_{50}$ of about 10,000 nM or less. In some embodiments, the compound of the invention can have an $IC_{50}$ of about 7,500 nM or less. In some embodiments, the compound of the invention can have an $IC_{50}$ of about 5,000 nM or less. In some embodiments, the compound of the invention can have an $IC_{50}$ of about 2,500 nM or less. In some embodiments, the compound of the invention can have an $IC_{50}$ of about 1,000 nM or less. In some embodiments, the compound of the invention can have an $IC_{50}$ of about 750 nM or less. In some embodiments, the compound of the invention can have an $IC_{50}$ of about 500 nM or less. In some embodiments, the compound of the invention can have an $IC_{50}$ of about 250 nM or less. In some embodiments, the compound of the invention can have an $IC_{50}$ of about 225 nM or less. In some embodiments, the compound of the invention can have an $IC_{50}$ of about 200 nM or less. In some embodiments, the compound of the invention can have an $IC_{50}$ of about 150 nM or less. In some embodiments, the compound of the invention can have an $IC_{50}$ of about 125 nM or less. In some embodiments, the compound of the invention can have an $IC_{50}$ of about 100 nM or less. In some embodiments, the compound of the invention can have an $IC_{50}$ of about 75 nM or less. In some embodiments, the compound of the invention can have an $IC_{50}$ of about 50 nM or less. In some embodiments, the compound of the invention can have an $IC_{50}$ of about 40 nM or less.

In some embodiments, the compound of the invention can have an $IC_{50}$ for a molluscum contagiosum virus of from about 20 nM to about 1,000 nM. In some embodiments, the compound of the invention can have an $IC_{50}$ of from about 20 nM to about 750 nM. In some embodiments, the compound of the invention can have an $IC_{50}$ of from about 20 nM to about 500 nM. In some embodiments, the compound of the invention can have $IC_{50}$ of from about 20 nM to about 250 nM. In some embodiments, the compound of the invention can have an $IC_{50}$ of from about 20 nM to about 225 nM. In some embodiments, the compound of the invention can have an $IC_{50}$ of from about 20 nM to about 200 nM. In some embodiments, the compound of the invention can have an $IC_{50}$ of from about 20 nM to about 150 nM. In some embodiments, the compound of the invention can have an $IC_{50}$ of from about 20 nM to about 125 nM. In some embodiments, the compound of the invention can have an $IC_{50}$ of from about 20 nM to about 100 nM. In some embodiments, the compound of the invention can have an $IC_{50}$ of from about 20 nM to about 75 nM. In some embodiments, the compound of the invention can have an $IC_{50}$ of from about 20 nM to about 50 nM.

In some embodiments, the compound of the invention can have an $IC_{50}$ for a molluscum contagiosum virus of from about 30 nM to about 1,000 nM. In some embodiments, the compound of the invention can have an $IC_{50}$ of from about 30 nM to about 750 nM. In some embodiments, the compound of the invention can have an $IC_{50}$ of from about 30 nM to about 500 nM. In some embodiments, the compound of the invention can have an $IC_{50}$ of from about 30 nM to about 250 nM. In some embodiments, the compound of the invention can have an $IC_{50}$ of from about 30 nM to about 225 nM. In some embodiments, the compound of the invention can have an $IC_{50}$ of from about 30 nM to about 200 nM. In some embodiments, the compound of the invention can have an $IC_{50}$ of from about 30 nM to about 150 nM. In some embodiments, the compound of the invention can have an $IC_{50}$ of from about 30 nM to about 125 nM. In some embodiments, the compound of the invention can have an $IC_{50}$ of from about 30 nM to about 100 nM. In some embodiments, the compound of the invention can have an $IC_{50}$ of from about 30 nM to about 75 nM. In some embodiments, the compound of the invention can have an $IC_{50}$ of from about 30 nM to about 50 nM.

In some embodiments, the compound of the present invention can have a selectivity index (SI) of about 120. In some embodiments, the compound of the present invention can have a selectivity index (SI) of about 150. In some embodiments, the compound of the present invention can have a selectivity index (SI) of about 370. In some embodiments, the compound of the present invention can have a selectivity index (SI) of about 570.

In some embodiments, the compound of the present invention can have a selectivity index (SI) of about 10 or more. In some embodiments, the compound of the present invention can have a selectivity index (SI) of about 50 or more. In some embodiments, the compound of the present invention can have a selectivity index (SI) of about 100 or more. In some embodiments, the compound of the present invention can have a selectivity index (SI) of about 150 or more. In some embodiments, the compound of the present invention can have a selectivity index (SI) of about 200 or more. In some embodiments, the compound of the present invention can have a selectivity index (SI) of about 250 or more. In some embodiments, the compound of the present invention can have a selectivity index (SI) of about 300 or more. In some embodiments, the compound of the present invention can have a selectivity index (SI) of about 350 or more. In some embodiments, the compound of the present invention can have a selectivity index (SI) of about 400 or more. In some embodiments, the compound of the present invention can have a selectivity index (SI) of about 450 or more. In some embodiments, the compound of the present invention can have a selectivity index (SI) of about 500 or more. In some embodiments, the compound of the present invention can have a selectivity index (SI) of about 600 or more. In some embodiments, the compound of the present invention can have a selectivity index (SI) of about 700 or more. In some embodiments, the compound of the present invention can have a selectivity index (SI) of about 800 or more. In some embodiments, the compound of the present invention can have a selectivity index (SI) of about 900 or more.

In some embodiments, the compound of the present invention can have a selectivity index (SI) of from about 50 to about 600. In some embodiments, the compound of the present invention can have a selectivity index (SI) of from about 100 to about 600. In some embodiments, the compound of the present invention can have a selectivity index (SI) of from about 150 to about 600. In some embodiments, the compound of the present invention can have a selectivity index (SI) of from about 200 to about 600. In some embodiments, the compound of the present invention can have a selectivity index (SI) of from about 250 to about 600. In some embodiments, the compound of the present invention can have a selectivity index (SI) of from about 300 to about 600. In some embodiments, the compound of the present invention can have a selectivity index (SI) of from about 350 to about 600. In some embodiments, the compound of the present invention can have a selectivity index (SI) of from about 400 to about 600. In some embodiments, the compound of the present invention can have a selectivity index (SI) of from about 450 to about 600. In some embodiments, the compound of the present invention can have a selectivity index (SI) of from about 500 to about 600.

In some embodiments, the compound of the present invention can have a binding efficiency index (BEI) of about 15. In other embodiments, the compound of the invention can have a binding efficiency index of about 17. In other embodiments, the compound of the invention can have a binding efficiency index of about 18. In other embodiments, the compound of the invention can have a binding efficiency index of about 19. In other embodiments, the compound of the invention can have a binding efficiency index of about 20.

In some embodiments, the compound of the invention can have a binding efficiency index of about 10 or more. In some embodiments, the compound of the invention can have a binding efficiency index of about 12 or more. In some embodiments, the compound of the invention can have a binding efficiency index of about 14 or more. In some embodiments, the compound of the invention can have a binding efficiency index of about 15 or more. In some embodiments, the compound of the invention can have a binding efficiency index of about 16 or more. In some embodiments, the compound of the invention can have a binding efficiency index of about 17 or more. In some embodiments, the compound of the invention can have a binding efficiency index of about 18 or more. In some embodiments, the compound of the invention can have a binding efficiency index of about 19 or more. In some embodiments, the compound of the invention can have a binding efficiency index of about 20 or more. In other embodiments, the compound of the invention can have a binding efficiency index of about 21 or more. In some embodiments, the compound of the invention can have a binding efficiency index of about 22 or more. In some embodiments, the compound of the invention can have a binding efficiency index of about 23 or more. In some embodiments, the compound of the invention can have a binding efficiency index of about 24 or more. In some embodiments, the compound of the invention can have a binding efficiency index of about 25 or more.

The present invention provides methods of inhibiting, treating, or abrogating a molluscum contagiosum virus infection in a subject in need thereof; inhibiting replication of a molluscum contagiosum virus; inhibiting activity of a molluscum contagiosum virus DNA polymerase; and decreasing processivity of a molluscum contagiosum virus DNA polymerase, comprising contacting a molluscum contagiosum virus with a compound of the present invention.

In certain embodiments, the present invention provides methods of treating a molluscum contagiosum virus infection in an animal and/or subject comprising administering to an animal and/or subject a compound of the present invention.

In certain embodiments, the present invention provides methods of abrogating a molluscum contagiosum virus infection in an animal and/or subject comprising administering to an animal and/or subject a compound of the present invention. In some embodiments, administering the compound of the present invention to the subject is performed by administering the compound to the subject topically.

The present invention further provides a composition comprising a compound of the invention described herein, for example, a compound of formula (I)-(XIV), or a pharmaceutically acceptable salt thereof, and at least one pharmaceutically acceptable carrier.

The present invention, in some embodiments, provides a composition that includes a compound of formula (I), in which variables $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and $R^{15}$ are as defined anywhere herein, or a pharmaceutically acceptable salt thereof, and at least one pharmaceutically acceptable carrier.

In some embodiments, the present invention provides a composition comprising a compound of formula (II) in which variables $R^1$, $R^2$, $R^3$, $R^4$, $R^5$, $R^6$, $R^7$, $R^8$, $R^9$, $R^{10}$, $R^{11}$, $R^{12}$, and $R^{13}$ are as defined anywhere herein, or a pharmaceutically acceptable salt thereof, and at least one pharmaceutically acceptable carrier.

In some embodiments, the present invention provides a composition comprising a compound of formula (III) in which variables $R^1$, $R^2$, $R^3$, $R^4$, $R^5$, $R^6$, $R^7$, $R^8$, and $R^9$ are as defined anywhere herein, or a pharmaceutically acceptable salt thereof, and at least one pharmaceutically acceptable carrier.

In some embodiments, the present invention provides a composition comprising a compound of formula (IV) in which variables $R^6$, $R^7$, $R^8$, $R^9$, $R^{10}$, $R^{13}$, $R^{12}$, and $R^{13}$ are as defined anywhere herein, or a pharmaceutically acceptable salt thereof, and at least one pharmaceutically acceptable carrier.

The present invention, in some embodiments, provides a composition that includes a compound of formula (V), in which variables $R^1$, $R^2$, $R^3$, $R^4$, $R^5$, $R^{10}$, $R^{11}$, $R^{12}$, and $R^{13}$ are as defined anywhere herein, or a pharmaceutically acceptable salt thereof, and at least one pharmaceutically acceptable carrier.

In some embodiments, the present invention provides a composition comprising a compound of formula (VI) in which variables $R^6$, $R^7$, $R^8$, and $R^9$ are as defined anywhere herein, or a pharmaceutically acceptable salt thereof, and at least one pharmaceutically acceptable carrier.

In some embodiments, the present invention provides a composition comprising a compound of formula (VII) in which variables $R^1$, $R^2$, $R^3$, $R^4$, $R^5$, and $R^6$are as defined anywhere herein, or a pharmaceutically acceptable salt thereof, and at least one pharmaceutically acceptable carrier.

In some embodiments, the present invention provides a composition comprising a compound of formula (VIII) in which variables $R^{10}$, $R^{11}$, $R^{12}$, and $R^{13}$are as defined anywhere herein, or a pharmaceutically acceptable salt thereof, and at least one pharmaceutically acceptable carrier.

In some embodiments, the present invention provides a composition comprising a compound of formula (IX) in which variables A, Z, Y, and $R^{14}$ are as defined anywhere herein, or a pharmaceutically acceptable salt thereof, and at least one pharmaceutically acceptable carrier.

In some embodiments, the present invention provides a composition comprising a compound of formula (X) in which variables Y, $R^1$, $R^2$, $R^3$, $R^4$, $R^5$, $R^6$, $R^7$, $R^8$, $R^9$, and $R^{14}$ are as defined anywhere herein, or a pharmaceutically acceptable salt thereof, and at least one pharmaceutically acceptable carrier.

In some embodiments, the present invention provides a composition comprising a compound of formula (XI) in which variables $R^1$, $R^2$, $R^3$, $R^4$, $R^5$, $R^6$, $R^7$ , $R^8$, and $R^9$ are as defined anywhere herein, or a pharmaceutically acceptable salt thereof, and at least one pharmaceutically acceptable carrier.

In some embodiments, the present invention provides a composition comprising a compound of formula (XII) in which variables Y, $R^1$, $R^2$, $R^3$, $R^4$, $R^5$, $R^7$, $R^8$, $R^9$, and $R^{14}$ are as defined anywhere herein, or a pharmaceutically acceptable salt thereof, and at least one pharmaceutically acceptable carrier.

In some embodiments, the present invention provides a composition comprising a compound of formula (XIII) in which variables $R^1$, $R^2$, $R^3$, $R^4$, $R^5$, $R^6$, $R^7$, $R^8$, $R^9$ , $R^{10}$, $R^{11}$, $R^{12}$, $R^{13}$, $R^{14}$, and $R^{16}$ are as defined anywhere herein, or a pharmaceutically acceptable salt thereof, and at least one pharmaceutically acceptable carrier.

In some embodiments, the present invention provides a composition comprising a compound of formula (XIV) in which variables $R^1$, $R^2$, $R^3$, $R^4$, $R^5$, $R^7$, $R^8$, $R^9$, $R^{10}$, $R^{11}$, $R^{12}$, $R^{13}$, $R^{14}$, and $R^{16}$ are as defined anywhere herein, or a pharmaceutically acceptable salt thereof, and at least one pharmaceutically acceptable carrier.

In some embodiments, the compounds of this invention are formulated into a pharmaceutical dosage form. In certain embodiments, the pharmaceutical dosage form further comprises pharmaceutically acceptable carriers, excipients, emollients, stabilizers, etc., as are known in the pharmaceutical industry. In certain embodiments, the pharmaceutical dosage form is formulated for topical administration. In some embodiments the pharmaceutical dosage will include other active agents such immune system modifiers. In another embodiment, other compounds for stabilizing, preserving, the formulation and the like, but are not involved directly in the therapeutic effect of the indicated active ingredient, are included.

In certain embodiments, the pharmaceutical compositions containing the compounds as described herein are administered to a subject topically. In certain embodiments, the pharmaceutical compositions containing the compounds as described herein are formulated for topical administration. In certain embodiments, the pharmaceutical compositions containing the compounds as described herein are administered to a subject by any method known to a person skilled in the art, such as parenterally, paracancerally, transmucosally, transdermally, intramuscularly, intravenously, intradermally, subcutaneously, intraperitonealy, intraventricularly, intracranially, intravaginally or intratumorally.

Various embodiments of dosage ranges are contemplated by this invention. In one embodiment, the dosage of the compounds as described herein is in the range of 0.1-100 mg/day. In another embodiment, the dosage is in the range of 0.1-50 mg/day. In another embodiment, the dosage is in the range of 0.1-20 mg/day. In another embodiment, the dosage is in the range of 0.1-10 mg/day. In another embodiment, the dosage is in the range of 0.1-5 mg/day. In another embodiment, the dosage is in the range of 0.5-5 mg/day.

For topical administration, embodiments of the invention may be formulated in the form of a lotion, cream, serum, spray, aerosol, cake, ointment, essence, gel, paste, patch, pencil, towelette, mask, stick, foam, elixir, concentrate, and the like form.

If the preferred mode is administered orally, in another embodiment, a unit dosage form comprises tablets, capsules, lozenges, chewable tablets, suspensions, emulsions and the like. In certain embodiments, such unit dosage forms comprise a safe and effective amount of the desired compound, or compounds, each of which is in another embodiment, from about 0.5 or 10 mg to about 300 mg/70 kg, or in another embodiment, about 0.5 or 10 mg to about 210 mg/70 kg. In certain embodiments, the pharmaceutically-acceptable carrier suitable for the preparation to of unit dosage forms for peroral administration is well-known in the art. In certain embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In certain embodiments, glidants such as silicon dioxide are used to improve flow characteristics of the powder-mixture. In certain embodiments, coloring agents, such as the FD&C dyes, are added for appearance. In certain embodiments, sweeteners and flavoring agents, such as aspartame, saccharin, menthol, peppermint, and fruit flavors, are useful adjuvants for chewable tablets. In certain embodiments, capsules typically comprise one or more solid diluents disclosed above. In certain embodiments, the selection of carrier components depends on secondary considerations like taste, cost, and shelf stability, which are not critical for the purposes of this invention, and are readily made by a person skilled in the art.

In certain embodiments, peroral compositions comprise liquid solutions, emulsions, suspensions, and the like. In certain embodiments, the pharmaceutically-acceptable carriers suitable for preparation of such compositions are well known in the art. In certain embodiments, liquid oral compositions comprise, in certain embodiments, from about 0.012% to about 0.933% of the desired compound or compounds, or in another embodiment, from about 0.033% to about 0.7%.

In another embodiment, the dosage is 10-20 μg/tablet. In another embodiment, the dosage is 20-30 μg/tablet. In another embodiment, the dosage is 20-40 μg/tablet. In another embodiment, the dosage is 30-60 μg/tablet. In another embodiment, the dosage is 40-80 μg/tablet. In another embodiment, the dosage is 50-100 μg/tablet. In another embodiment, the dosage is 50-150 μg/tablet. In another embodiment, the dosage is 100-200 μg/tablet. In another embodiment, the dosage is 200-300 μg/tablet. In another embodiment, the dosage is 300-400 μg/tablet. In another embodiment, the dosage is 400-600 μg/tablet. In another embodiment, the dosage is 500-800 μg/tablet. In another embodiment, the dosage is 800-1000 μg/tablet. In another embodiment, the dosage is 1000-1500 μg/tablet. In another embodiment, the dosage is 1500-2000 μg/tablet. In another embodiment, the dosage is 2-3 mg/tablet. In another embodiment, the dosage is 2-5 mg/tablet. In another embodiment, the dosage is 2-10 mg/tablet. In another embodiment, the dosage is 2-20 mg/tablet. In another embodiment, the dosage is 2-30 mg/tablet. In another embodiment, the dosage is 2-50 mg/tablet. In another embodiment, the dosage is 2-80 mg/tablet. In another embodiment, the dosage is 2-100 mg/tablet. In another embodiment, the dosage is 3-10 mg/tablet. In another embodiment, the dosage is 3-20 mg/tablet. In another embodiment, the dosage is 3-30 mg/tablet. In another embodiment, the dosage is 3-50 mg/tablet. In another embodiment, the dosage is 3-80 mg/tablet. In another embodiment, the dosage is 3-100 mg/tablet. In another embodiment, the dosage is 5-10 mg/tablet. In another embodiment, the dosage is 5-20 mg/tablet. In another embodiment, the dosage is 5-30 mg/tablet. In another embodiment, the dosage is 5-50 mg/tablet. In another embodiment, the dosage is 5-80 mg/tablet. In another embodiment, the dosage is 5-100 mg/tablet. In another embodiment, the dosage is 10-20 mg/tablet. In another embodiment, the dosage is 10-30 mg/tablet. In another embodiment, the dosage is 10-50 mg/tablet. In another embodiment, the dosage is 10-80 mg/tablet. In another embodiment, the dosage is 10-100 mg/tablet.

In some embodiments, compositions for use in the methods of this invention comprise solutions or emulsions, which in another embodiment are aqueous solutions or emulsions comprising a safe and effective amount of a compound as described herein and in yet another embodiment, other compounds. In one embodiment, such compositions comprise from about 0.01% to about 10.0% w/v of a subject compound, more preferably from about 0.1% to about 5.0, which in another embodiment, is used for the systemic delivery of compounds by a route known to one skilled in the art.

In certain embodiments, the compositions comprise dry powders. In certain embodiments, compositions are formulated for atomization and/or inhalation administration. In certain embodiments, such compositions are contained in a container with attached atomizing means.

Further, in another embodiment, the pharmaceutical compositions are administered by intravenous, intra-arterial, or intramuscular injection of a liquid preparation. In certain embodiments, suitable liquid formulations include solutions, suspensions, dispersions, emulsions, oils and the like. In another embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

In another embodiment, the active compound is delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327).

In another embodiment, the pharmaceutical composition delivered in a controlled to release system is formulated for intravenous infusion, implantable osmotic pump, transdermal patch, liposomes, or other modes of administration. In another embodiment, a pump may be used (see Langer, supra; Sefton, CRC Crit. Ref. *Biomed. Eng.* 14:201 (1987); Buchwald et al., Surgery 88:507 (1980); Saudek et al., *N. Engl. J. Med.* 321:574 (1989). In another embodiment, polymeric materials are used. In yet one embodiment, a controlled release system is placed in proximity to the therapeutic target, i.e., the brain, thus requiring only a fraction of the systemic dose (see, e.g., Goodson, in *Medical Applications of Controlled Release,* supra, vol. 2, pp. 115-138 (1984). Other controlled release systems are discussed in the review by Langer (*Science* 249:1527-1533 (1990).

The preparation of pharmaceutical compositions which contain active components is well understood in the art, for example by mixing, granulating, or tablet-forming processes. In certain embodiments, the active therapeutic ingredients are mixed with excipients which are pharmaceutically acceptable and compatible with the active ingredient. In certain embodiments, for oral administration, the compounds as described herein or their physiologically tolerated derivatives such as salts, esters, N-oxides, and the like and additional therapeutic agent or agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

In certain embodiments, an active component as described herein is formulated into the composition as neutralized pharmaceutically acceptable salt forms. In certain embodiments, pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. In certain embodiments, salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In certain embodiments, for use in medicine, the salts of the compounds as described herein will be pharmaceutically acceptable salts. In certain embodiments, other salts may, however, be useful in the preparation of the compounds used in the methods described herein, or of their pharmaceutically acceptable salts. In certain embodiments, suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In certain embodiments, the compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acids and bases to adjust the pH of these aqueous compositions as needed. In certain embodiments, the compositions may also comprise local anesthetics or other actives. In certain embodiments, the compositions are used as sprays, mists, drops, and the like.

In certain embodiments, substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. In certain embodiments, the choice of a pharmaceutically-acceptable carrier to be used in conjunction with the compound is basically determined by the way the compound is to be administered. In certain embodiments, wherein the subject compound is to be injected, the preferred pharmaceutically-acceptable carrier is sterile, physiological saline, with a blood-compatible suspending agent, the pH of which has been adjusted to about 7.4.

In certain embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents(e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In certain embodiments, typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. AVICEL™, RC-591), tragacanth and sodium alginate; typical wetting agents include lecithin and polyethylene oxide sorbitan (e.g. polysorbate 80). In certain embodiments, typical preservatives include methyl paraben and sodium benzoate. In certain embodiments, peroral liquid compositions also contain one or more components such as sweeteners, flavoring agents and colorants disclosed above.

In certain embodiments, dry powder compositions may comprise propellants such as chlorofluorocarbons 12/11 and 12/114, or, in another embodiment, other fluorocarbons, nontoxic volatiles; solvents such as water, glycerol and ethanol, these include co-solvents as needed to solvate or suspend the active; stabilizers such as ascorbic acid, sodium metabisulfite; preservatives such as cetylpyridinium chloride and benzalkonium chloride; tonicity adjustors such as sodium chloride; buffers; and flavoring agents such as sodium saccharin.

In certain embodiments, the compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In certain embodiments, also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In certain embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). In certain embodiments, such modifications may also increase the compounds solubility in aqueous solution, eliminate aggregation, enhance the physical and chemical stability of the compound, and greatly reduce the immunogenicity and reactivity of the compound. In certain embodiments, the desired in vivo biological activity may be achieved by the administration of such polymer-compound abducts less frequently or in lower doses than with the unmodified compound.

In certain embodiments, the compounds of the invention are administered as the sole active pharmaceutical agent, they can also be used in combination with one or more other compound as described herein, and/or in combination with other agents used in the treatment and/or prevention of diseases, disorders and/or conditions, associated with a poxvirus infection, as will be understood by one skilled in the art. In another embodiment, the compounds as described herein are administered sequentially with one or more such agents to provide sustained therapeutic and prophylactic effects. In another embodiment, the compounds may be administered via different routes, at different times, or a combination thereof. It is to be understood that any means of administering combined therapies which include the compounds of this invention are to be considered as part of this invention.

In another embodiment, the additional active agents are generally employed in therapeutic amounts as indicated in the PHYSICIANS' DESK REFERENCE (PDR) 53rd Edition (1999), which is incorporated herein by reference, or such therapeutically useful amounts as would be known to one of ordinary skill in the art. In another embodiment, the compounds of the invention and the other therapeutically active agents are administered at the recommended maximum clinical dosage or at lower doses. In certain embodiments, dosage levels of the active compounds in the compositions of the invention may be varied to obtain a desired therapeutic response depending on the route of administration, severity of the disease and the response of the patient. In another embodiment, the combination is administered as separate compositions or in other embodiments as a single dosage form containing both agents. In certain embodiments, when administered as a combination, the therapeutic agents is formulated, in another embodiment, as separate compositions that are given at the same time or different times, or in other embodiments the therapeutic agents are given as a single composition.

In certain embodiments, the compositions and methods described herein are employed in the treatment of humans. In certain embodiments, the compositions and methods described herein are employed in the treatment of domesticated mammals which are maintained as human companions (e.g., dogs, cats, horses), which have significant commercial value (e.g., dairy cows. beef cattle, sporting animals), which have significant scientific value (e.g., captive or free specimens of endangered species), or which otherwise have value.

The following examples are presented in order to more fully illustrate the preferred embodiments of the invention. They should in no way be construed, however, as limiting the broad scope of the invention.

EXAMPLES

Materials and Methods

Cell culture. Rabbit kidney (RK) cells were maintained in MEM supplemented with 10% fetal bovine serum and antibiotic/antimycotic mix (Invitrogen). The media to grow the RK-D4R cells was further supplemented with 400 ug/ml of hygromycin B. African green monkey epithelial cells (BSC-1) were maintained in DMEM supplemented with 10% fetal bovine serum and 10 μg/mL gentamicin.

Cloning of MCV E9L, A20R, and D4R. The MCV E9L (mE9), A20R (mA20), and D4R (mD4) genes were PCR-amplified from genomic DNA obtained from tissue samples (kindly provided by R. M. Buller, Saint Louis University School of Medicine) using the following primer sets: E9L forward 5'-AGAAAGCTTGCCATGGAGATCCGG-TGTCTCAA (SEQ ID NO: 1) and reverse 5'-TCTCTCTAGACTAGTTCGAGAAGACGGGGCGCAC (SEQ ID NO: 2); A20R forward 5'-GAGAAAGCTTGCCATG-GCCAAGGAGCCCGAT (SEQ ID NO: 3) and reverse 5'-TCTCTCTAGATTACTTCTCGGCGCTGGAC (SEQ ID NO: 4); D4R forward 5'-GAGAAAGCTTGCCATGG-TGCGCGAGCGCGCGCT (SEQ ID NO: 5) and reverse 5'-TCTCTCTAGAGGGGTACGAAGCCCT (SEQ ID NO: 6). PCR was performed using Herculase Enhanced DNA Pol according to the manufacture's recommendation (Agilent Technologies, Inc.) with the addition of 1 M betaine and 5% DMSO for each reaction. Cloning into pcDNA3.1(+) plasmid (Invitrogen) was accomplished using the HindIII (forward primer, underlined) and XbaI (reverse primer, underlined) sites. The Kozak sequence (GCCATGG) was included within the forward primers to allow for proper initiation of translation. All inserts were confirmed by DNA sequencing. The VV E9L (vE9), A20R (vA20), and D4R (vD4) genes were cloned as described previously.

Protein expression and purification. The MCV and VV E9, A20, and D4 [$^{35}$S]Cys/Met labeled proteins, respectively, were generated from recombinant pcDNA3.1 using the TNT T7 coupled reticulocyte lysate system (Promega). Labeled proteins were separated on SDS gel and visualized by autoradiography. To express N-terminally 6His-tagged mD4, mD4R gene was amplified by PCR using primers 5'mD4 5'-AGACATATGCTGCGCGAGCGCGCGCTG (SEQ ID NO: 7) and 3'mD4 5'-AGAGGATCCTAAAGGGGTACGAAGCCCTG (SEQ ID NO: 8) and cloned into the NdeI and BamHI sites of an *E. coli* expression vector pET-15b (Novagen). 6His-mD4 protein was expressed in *E. coli* Rosetta (DE3) strain (EMD Millipore) by induction with 0.6 mM IPTG overnight at 17° C. Total protein was extracted from the cells by treatment with 0.25 mg/ml lysozyme for 1 h at 4° C. in phosphate buffer (50 mM phosphate buffer, pH 7.1, 400 mM NaCl, 5% glycerol,) containing 0.1% Triton X-100, 0.1% Tween 20, and 0.5 mM PMSF, followed by 3× freeze/thaw and sonication. After centrifugation, the supernatant was loaded onto a Talon cobalt resin column (Clontech), followed by thorough wash with the above phosphate buffer containing 20 mM imidazole. 6His-mD4 protein was eluted with 200 mM imidazole, and then further purified by Superdex 200 gel filtration with 25 mM phosphate buffer (pH 6.8) containing 200 mM NaCl and 5% glycerol. The in vitro translated and *E. coli*-expressed proteins were used for processive DNA synthesis assays as described below.

Processive DNA synthesis assays. Processive DNA synthesis was assessed by two types of assays: the Rapid Plate Assay and the M13 assay. The Rapid Plate Assay was performed as previously described. Briefly, a 5'-biotinylated 100-nucleotide template that contains adenines only at its 5' distal end was annealed with a 15-nucleotide primer to its 3' end and attached to streptavidin-coated 96-plate wells (Roche Applied Science). DNA synthesis was carried out in 50 μL reaction mixture containing 100 mM $(NH)_2SO_4$, 20 mM Tris-HCl (pH 7.5), 3 mM $MgCl_2$, 0.1 mM EDTA, 0.5 mM DTT, 2% glycerol, 40 μg/ml BSA, 5 μM dATP, 5 μM dCTP, 5 μM dGTP, 1 μM digoxigenin-11-dUTP, and E9/A20/D4 proteins. The TNT reticulocyte lysate or in vitro translated luciferase was used as a negative control. After incubation at 37° C. for 30 min, the plate was washed extensively with phosphate-buffered saline (PBS). The wells were then incubated with anti-digoxigenin-peroxidase antibody (Roche) for 1 h at 37° C., followed by washing with PBS. The substrate 2,2'-azino-bis(3-ethylbenzthiazoline)-sulfonate (Roche) was added, and plates were gently rocked to allow color development. DNA synthesis was quantified by measuring the absorbance of each reaction at 405 nm with a microplate reader (Tecan). Experiments were conducted in triplicate and independently repeated at least twice.

The M13 assay was conducted as described. Briefly, the reaction mixture (50 μL) contained 45 fmol of primed M13mp18 single-stranded DNA, 100 mM $(NH_4)_2SO_4$, 10 mM Tris-HCl pH 7.5, 8 mM $MgCl_2$, 0.1 mM EDTA, 5 mM DTT, 40 μg/ml BSA, 4% Glycerol, 60 μM each dATP, dGTP and dTTP and 20 μM [$\alpha$-$^{32}$P] dCTP. After incubation at 37° C. for 1 h, the reaction was stopped by adding 6x loading dye containing 200 mM NaOH. Products were fractionated on a 1.3% alkaline agarose gel and visualized by autoradiography.

Protein pull-down assay. 1.5 μg purified 6His-mD4 was incubated with 10 μL in vitro translated [$^{35}$S]-labeled A20, 15 μL Talon cobalt beads (pretreated with 5% BSA) and 300 μL PBS-NP buffer (PBS with 0.2% NP40) for 2 hours at 4° C. The beads were washed four times in PBS-NP buffer (15 min each). Pulled-down proteins were separated on SDS gel and visualized by autoradiography.

Thermal shift assay. Thermal shift (differential scanning fluorimetry) assay was performed as previously described. Briefly, 5 μM purified 6His-mD4 was mixed with compounds in thin-wall PCR 96-plate wells at 20 μL total volume containing 25 mM phosphate buffer (pH 6.8), 0.2 M NaCl, 2.5% glycerol, 2% DMSO, 0.005% (w/v) Triton-X100, and 1× Sypro Orange. Fluorescence intensities were monitored using the Applied Biosystems 7500 Fast Real-Time PCR system (Carlsbad, Calif.) at 582 nm from 25-80 ° C. at a rate of 1° C./min To generate melting temperature (Tm), protein melting curves were plotted on GraphPad Prism and fitted to the Boltzmann sigmoidal model. Thermal shift ($\Delta T_m$) is the difference between the 2% DMSO mock-treatment and inhibitor treatment. All experiments were duplicated and repeated independently.

Construction, isolation, and characterization of mD4-VV hybrid virus and vD4-VV rescue virus. The vaccinia virus vD4-ZG lacking a functional D4R gene (VVΔD4R), a rabbit kidney cell line stably expressing the vaccinia D4 protein (RK-D4R), and plasmid pER, which contains D4R sequences flanked by D3R and D5R sequences, were gifts of F. G. Falkner and provided to us by B. Moss.

To construct a plasmid to generate the mD4-VV hybrid virus, mD4R gene was amplified using primers 5'mD4-EcoRI 5'-GTGGAATTCAATGCTGCGCGAG-CGCGCGCTG (SEQ ID NO: 9) and 3'mD4-Hind3 5'-GAG AAGCTTCTAAAGG- GGTACGAAGCCCTG (SEQ ID NO: 10), and subcloned into the EcoRI and HindIII sites of pER plasmid. This replaces vD4R with mD4R gene, but with the derived clone containing two start ATG codons (in bold, 5'-TATAATGAATTCAATGCTG (SEQ ID NO: 11)), of which the first one is from vD4R gene. To remove the vD4R start codon, site-directed mutagenesis was performed using a pair of complementary primer 5'-AAAGGTATCTAATTTGATATAATAAA GCCATGCTGCGCGAGCGCG (SEQ ID NO: 12), mutated nucleotide is in lower case and underlined nucleotides are mD4 sequences) to generate plasmid pER-mD4(ATG), which contains only the mD4R start codon and thus encodes wild-type mD4.

mD4-VV hybrid virus and vD4-VV rescue virus were generated by homologous recombination of pER-mD4 (ATG) and pER, respectively, by transfection of plasmids into RK-D4R cells infected with parental virus VVAD4R as previously described. After 48 hours, cells were harvested and virus released by freeze-thawing and sonication. Recombinant viruses were then isolated by infecting BSC-1 cells with the virus lysates from RK-D4R cells and successive plaque purifications of large plaques. The recombinant viruses were confirmed by PCR and sequencing. When compared to the mD4R sequence (VP0038088) in poxvirus.org, the mD4R sequence in the recombinant mD4R-VV hybrid virus (plaque #224a1-1) was an identical match. When compared to the D4R WR sequence (VP0042547) in poxvirus.org, the vD4R sequence in the recombinant vD4-VV rescue virus (plaque #225a1) contained an amino acid Asn instead of Lys at residue 150. This base change was also present in the starting plasmid pER.

Virus growth kinetics were measured on confluent BSC-1 cells in wells of 24-well plates infected at a multiplicity of infection (MOI) 0.05 pfu/cell with mD4-VV hybrid virus and vD4-VV rescue virus in quadruplicate. At various time points, media and cells were harvested and virus titers were determined.

Viral plaque reduction and cytotoxicity assays. Viral plaque reduction assay was performed using BSC-1 cells as previously described in triplicate, and independently repeated for compound 10. Briefly, cells were infected by adsorbing virus at 80 PFU/well in 100 μL of growth medium for 1 h in 48-well plate, followed by 16 h treatment with compounds. Cells were stained and plaques counted under dissecting microscope and data was plotted on GraphPad Prism. Cytotoxicity on BSC-1 cells was assessed by the lactate dehydrogenase assays (LDH) as previously reported.

Dot-blot hybridization. BSC-1 cells were grown to confluency by seeding $1.2\times10^5$ cells/well in a 24-well plate and incubated at 37° C. overnight. Cells were infected by adsorbing virus (~1 MOI) in 200 μL of growth medium for 1 h, followed by treatment with 65 μM compound 10. Cells were then collected at various time points. Viral DNA was extracted with 20 mM Tris buffer (pH 7.5) containing 20 mM EDTA, 0.5% (w/v) SDS and 0.5 mg/ml proteinase K and used for dot-blot hybridization as described previously. $^{32}$P-labeled vA20 DNA was used as a probe.

Example 1

Cloning and expression of the DNA Pol and PF of MCV. Based on sequence homology to vaccinia virus (VV), it is predicted that the MCV PF (mA20 and mD4) should enable the cognate mE9 DNA Pol to synthesize DNA processively.

Figure 1:
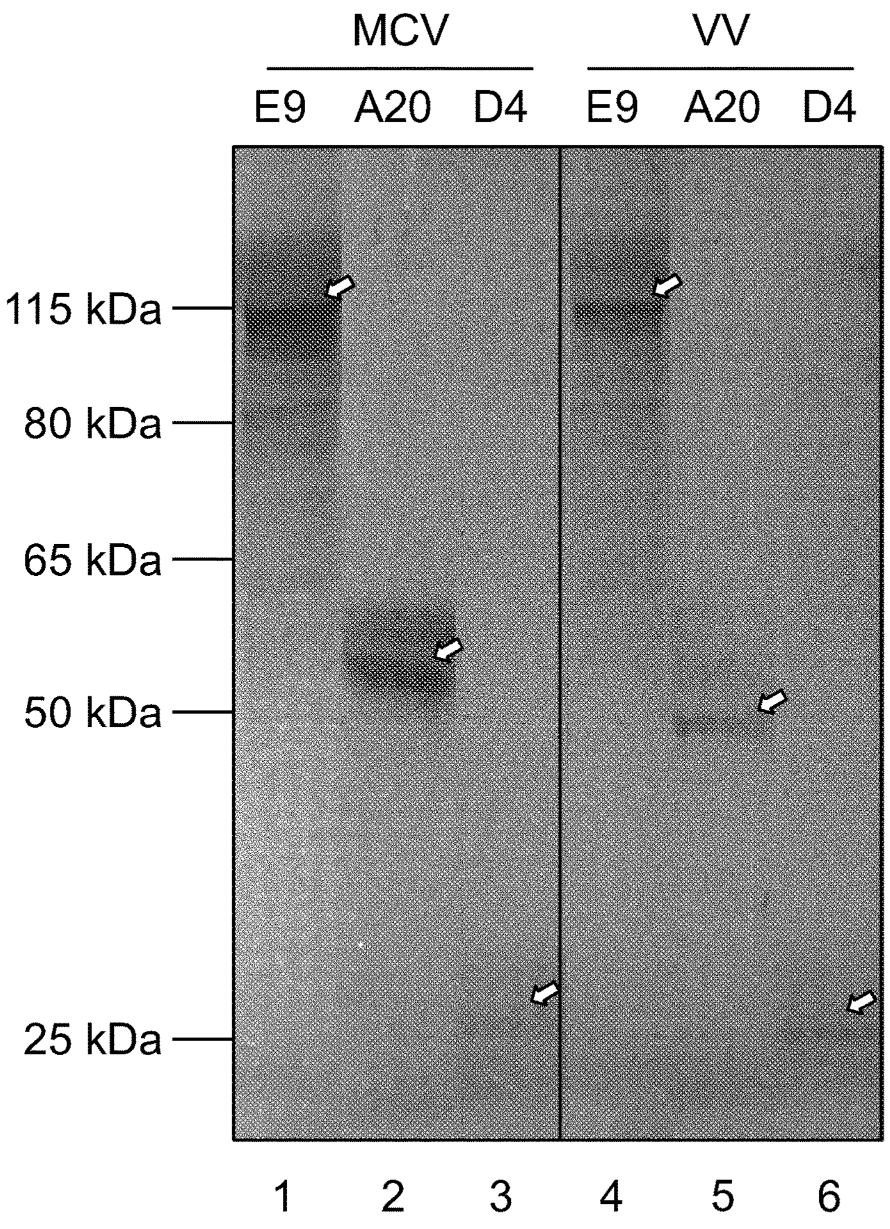
FIG. 1. In vitro translation of MCV and VV polymerases and processivity factors. The E9 to polymerases and the processivity factors D4 and A20 from the molluscum contagiosum and vaccinia viruses were in vitro translated from cloned plasmids and labeled with [$^{35}$S]Cys/Met. Proteins were fractionated on an SDS gel and visualized by autoradiography. Arrows indicate full-length proteins. Note that lanes from the original autoradiogram were rearranged for convenient comparison.
Figure 2:
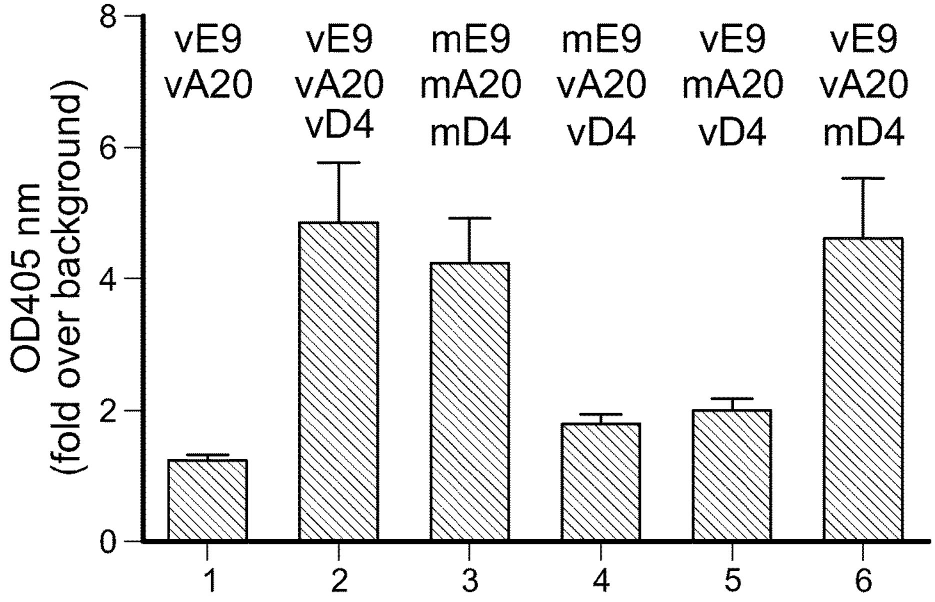
FIG. 2. mD4 can substitute vD4 in processive DNA synthesis. DNA synthesis was conducted with homologous and heterologous combinations of the E9 polymerases and the A20 and D4 processivity factors from VV and MCV using the Rapid Plate Assay. DNA synthesis was quantitated by the incorporation of dig-dUTP, which was detected by peroxidase-conjugated DIG-antibody (OD405 nm). The background OD value is arbitrarily set to 1. The data represent mean+SD from at least two independent experiments in triplicate.
Figure 3A:
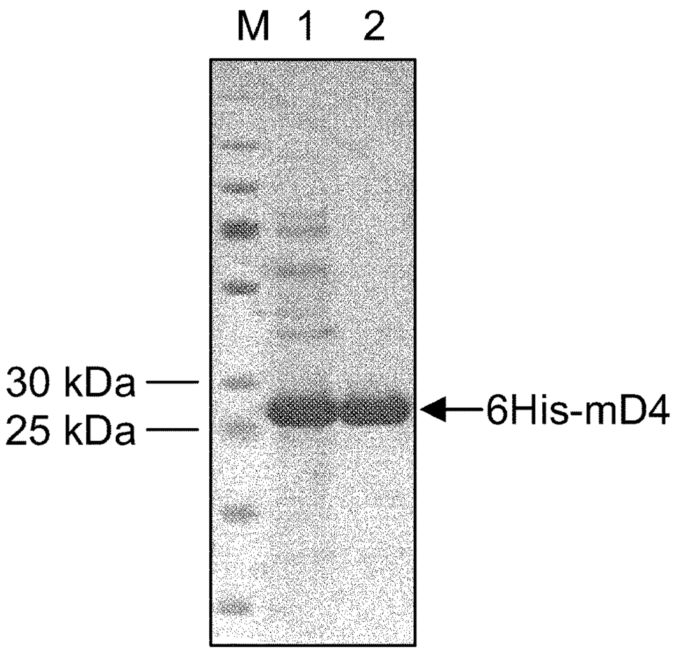
FIG. 3. Purified mD4 physically interacts with A20 from both MCV and VV. (A) Expression and purification of His-tagged mD4 from bacteria. N-terminal 6× His-tagged mD4 (6His-mD4) was induced in *E. coli* and purified using cobalt metal-affinity resins (lane 1), followed by gel filtration chromatography on Superdex 200 (lane 2). M indicates size markers. (B) Pull-down assay. Purified 6His-mD4 was incubated with in vitro translated [$^{35}$S]-labeled mA20 or vA20 and pulled-down by cobalt resins. Pulled-down proteins were separated on SDS gel and visualized by autoradiography. The input represents 5% of the radio-labeled proteins used for the pull-down assay.
Figure 3B:
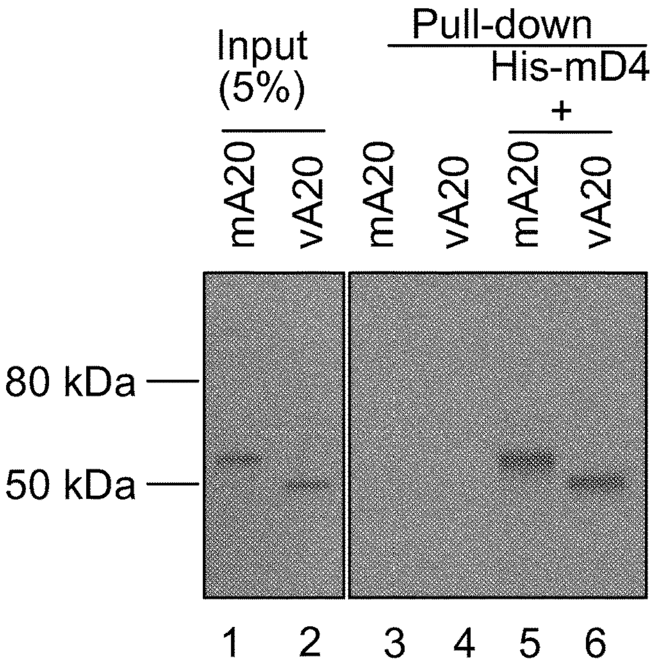
Figure 4:
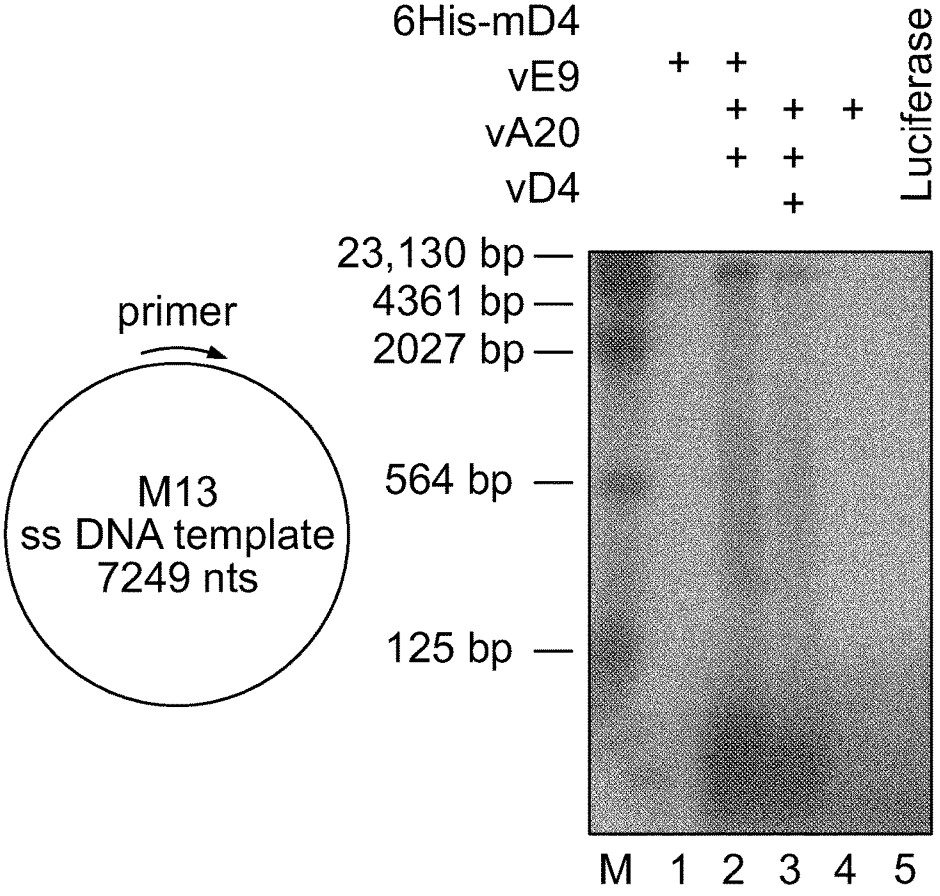
FIG. 4. Purified mD4 is functional in processive DNA synthesis. Full-length M13 DNA (7,249 nucleotides) was annealed to a primer (Left) and used as template for DNA synthesis with in vitro translated vE9, vA20 and either purified 6His-mD4 or in vitro translated vD4. The newly synthesized DNA products were fractionated on a 1.3% alkaline agarose gel and visualized by to autoradiography (Right). The 6His-mD4-dependent mixed triad (lane 2) was able to synthesize the 7,249 nucleotide full-length M13 DNA as did the VV triad (lane 3) which served as a positive control.
Figure 8:
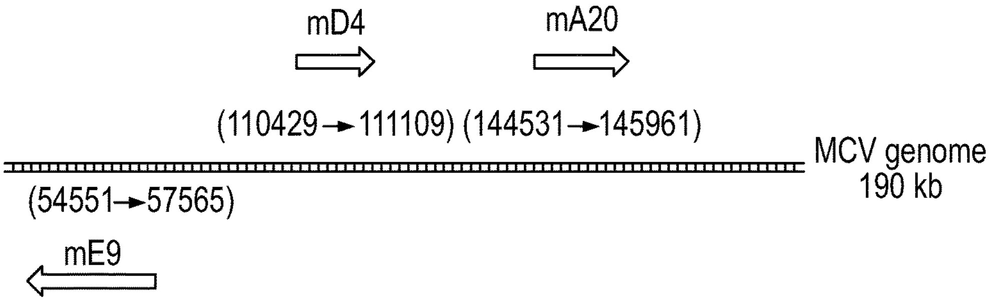
FIG. 8. The location of D4, A20 and E9 genes on the MCV genome. Indicated are the orientations (arrows) and the locations of the nucleotide coding regions (numbers) for the mD4 to and mA20 processivity factors and the mE9 DNA polymerase on the MCV genome.

In order to verify this assumption, these three MCV genes were first cloned from a clinical isolate obtained from an individual with MC (see FIG. 8 for the orientations and genomic positions of the coding regions for mE9, mA20 and mD4). The complete coding region of each MCV gene was amplified with primers that contained a translational Kozak sequence and HindIII and Xbal restrictions sites for insertion into pcDNA3.1(+). All clones were validated by DNA sequencing. When transcribed and translated in vitro, each of the cloned templates was able to generate a protein product of the predicted size (FIG. 1). These MCV proteins are similar in size to their corresponding counterparts of vaccinia virus (FIG. 1).

mE9, mD4 and mA20 perform processive DNA synthesis in the Rapid Plate Assay. In order to test for processive DNA synthesis of the MCV proteins (FIG. 1), the Rapid Plate Assay (RPA) was employed that measures nucleotide incorporation. The RPA consists of a 100 nucleotide template with a biotin moiety on its 5' end and a 15 nucleotide primer annealed to its 3' end. The annealed primer template is attached to streptavidin coated well of a 96-well plate. The addition of DNA Pol and PF cause incorporation of dNTPs and dig-dUTP that is recognized by digoxigenin (DIG) antibody coupled to HRP for colorimetric quantitation. This RPA has been successfully used to determine the strict requirement of all three members of the VV protein triad (vE9, vA20, vD4) in processive DNA synthesis. Indeed, omission of any member of this protein triad precludes processive DNA synthesis (see FIG. 2, compare bars 1 and 2). As shown in FIG. 2, the MCV mE9, mA20, and mD4 triad exhibited the same activity as the corresponding VV proteins (compare bars 2 and 3).

mD4 fully substitutes for vD4 to enable processive DNA synthesis in the Rapid Plate Assay. As shown in FIG. 2, mE9 and mA20 each can only poorly substitute for their VV counterparts to enable processive DNA synthesis (FIG. 2, bars 4 and 5). In strong contrast, mD4 is completely capable of substituting for vD4 (FIG. 2, compare bar 6 with bars 2, 3).

mD4 physically associates with mA20 or vA20. The VV processivity proteins vD4 and vA20 form a heterodimeric complex and are both required to enable DNA Pol to conduct extended DNA strand synthesis. It was important to demonstrate that the functional ability of mD4 to substitute for vD4 in processivity (FIG. 2) is related to its ability to bind vA20. Toward this end, 6His-tagged mD4 (6His-mD4) produced in *E. coli* was purified to homogeneity (FIG. 3A) for use in pull-down assays. As shown in FIG. 3B, 6His-mD4 was able to pull down in vitro translated mA20 and vA20, respectively. This result strongly supports the premise that the ability of mD4 to functionally substitute for vD4 involves the formation of the mD4/vA20 hetero-complex.

mD4 enables long-chain processive DNA synthesis in the M13 Assay. The RPA (FIG. 2) is reliable screening technology to evaluate processivity, but is limited to the maximum incorporation of nucleotides. In order to confirm that mD4 can completely substitute for vD4 in long-chain processive DNA synthesis, a more rigorous assay was employed using M13 single-strand DNA (7,249 nucleotides) as template. In this assay, the M13 template was annealed to a 30 nucleotide primer and incubated with dNTPs in the presence of vE9, vA20 and either vD4 or 6His-mD4. As shown in FIG. 4, neither 6His-mD4 alone (lane 1) or vE9 alone (lane 4) nor the negative control luciferase (lane 5), were capable of generating newly synthesized DNA from the M13 template. By contrast, the 6His-mD4, vA20 and vE9 triad was able to synthesize the 7,249 nucleotide full-length strand (lane 2). As a positive control, the VV-triad (vE9, vD4, vA20) was also shown to produce full-length M13 product (lane 3). Of note, the assay is not quantitative for signal-strength, since the synthetic source of each D4 protein was different, i.e., bacterial His-mD4 and in vitro translated vD4. These data clearly demonstrate that mD4 is capable of substituting for vD4 in processive DNA synthesis.

Compound 10 binds mD4 and blocks mD4-dependent processive DNA synthesis in vitro. From a previous high-throughput screening that examined the disruption of interaction between vD4 and the N-terminal domain of vA20, five small chemical compounds that can bind vD4 and inhibit VV DNA synthesis and infection were discovered (Nuth M, et al. 2011. *J. Med. Chem.* 54:3260-3267). The fact that mD4 can substitute for its VV counterpart vD4 (FIGS. 3 and 5), prompted us to inquire whether mD4 could also be targeted by these five compounds. To examine this possibility, the Thermofluor assay (differential scanning fluorimetry) was first employed. This assay can detect the binding of a small molecule to a protein by observing an increase in thermal stability ($T_m$). It is found that one of the five small molecules, compound 10 (4-({[2-(benzyloxy)phenyl]methyl}amino)phenol), was clearly able to bind mD4. As seen in FIG. 5A, purified 6His-mD4 exhibited a $T_m$ shift ($\Delta T_m$: 2.2° C.) in the presence of 10 μM compound 10 and an even greater $T_m$ shift ($\Delta T_m$: 3.3° C.) in the presence of 40 μM compound 10. This result suggests that compound 10 binds to a conserved region of vD4 and mD4.

To examine whether the binding of compound 10 to mD4 would inhibit its essential role as a PF in DNA synthesis, the RPA was employed that can quantitatively evaluate the potency ($IC_{50}$) of small chemical inhibitors for their abilities to block processive DNA synthesis. In order to be consistent with the M13 assay (FIG. 4), translated vE9, vA20 and bacterial 6His-mD4 were used. As shown in FIG. 5B, compound 10 was able to block DNA synthesis with an $IC_{50}$=28 μM. Taken together, these results indicate that compound 10 binds mD4 to disable it from functioning in processive DNA synthesis.

Figure 6A:
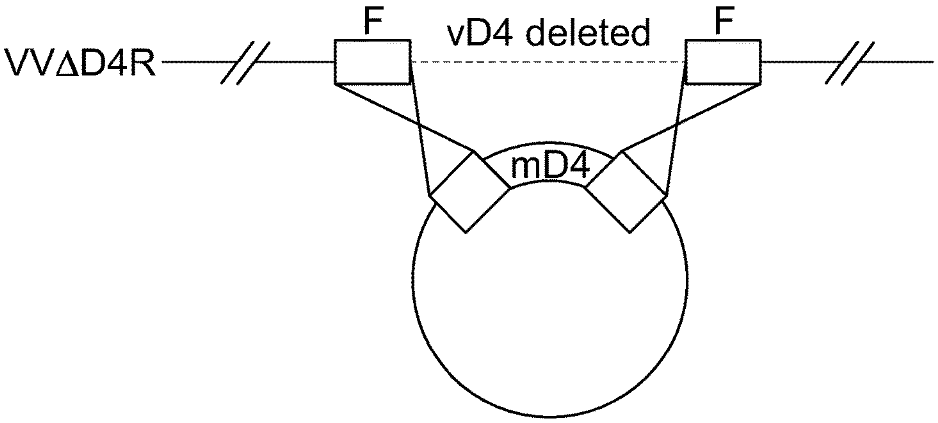
FIG. 6. Construction of a vaccinia hybrid virus containing mD4 of MCV. (A) Schematic of the construction of mD4-VV hybrid virus. The starting VV has vD4 deleted (VVDD4R). Cloned mD4 with vD4 flanking sequences was transfected into RK-D4R helper cells infected with VVΔD4R , in which the natural vD4 gene had been deleted. The mD4-VV hybrid virus was obtained through homologous recombination, plaque purified and the mD4 insert was verified by DNA sequencing. As a control, the vD4-VV rescue virus was similarly generated by using a vD4 plasmid. The boxes labeled F are vD4-flanking sequences. (B) Growth curves of mD4-VV and vD4-VV. BSC-1 cells were infected with mD4-VV and vD4-VV viruses (MOI~0.05 pfu/cell). At indicated time points, media and cells were harvested and virus titers were determined.
Figure 6B:
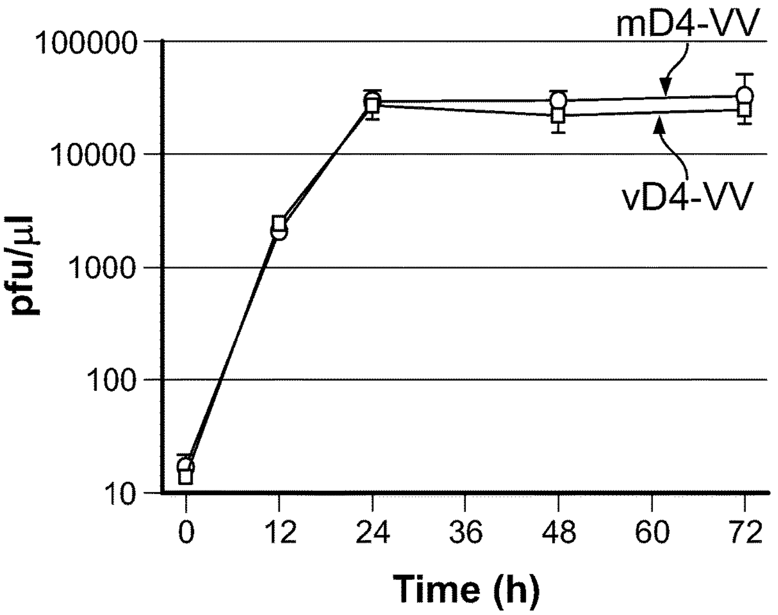

Constructing an mD4-VV hybrid virus to assay compounds that target mD4. To evaluate whether compound 10 is capable of blocking mD4 function in the context of a viral infection, the major impediment in discovering drugs that specifically target a critical function of MCV has been the inability to propagate this virus in all cell culture system attempted thus far. This obstacle has been circumvented by engineering a vaccinia hybrid virus (mD4-VV) in which vD4 is replaced by mD4 (FIG. 6). The rationale for electing this approach was our demonstration that mD4 can completely substitute for vD4 in processive DNA synthesis (FIGS. 3, 6, 8). A depiction of the how the mD4-VV virus was engineered is shown in FIG. 6A. Briefly, the mD4-VV hybrid virus was engineered from the VV D4 deletion mutant virus, VVΔD4R. The VVΔD4R virus (WR strain) can only be propagated on a complementing vD4-expressing rabbit kidney (RK) cell line and not in the normal RK (or BSC-1) cells. mD4 was introduced into VVΔD4R by homologous recombination as shown in FIG. 6A. The new mD4-VV hybrid virus was isolated by several rounds of plaque purification in BSC-1 cells. The amplified stock of mD4-VV hybrid virus was sequenced to verify that it encodes the complete and fully intact mD4 gene. As a positive control, the vD4 back was recombined into VVΔD4R to generate a rescue virus vD4-VV. FIG. 6B reveals that multi-step growth curves for mD4-VV hybrid virus and the positive control vD4-VV rescue virus are nearly identical when propagated on BSC-1 cells. Also, in BSC-1 cells, the mD4-VV hybrid virus produced plaques of similar size to those of the positive control virus vD4-VV (data not shown).

Figure 7A:
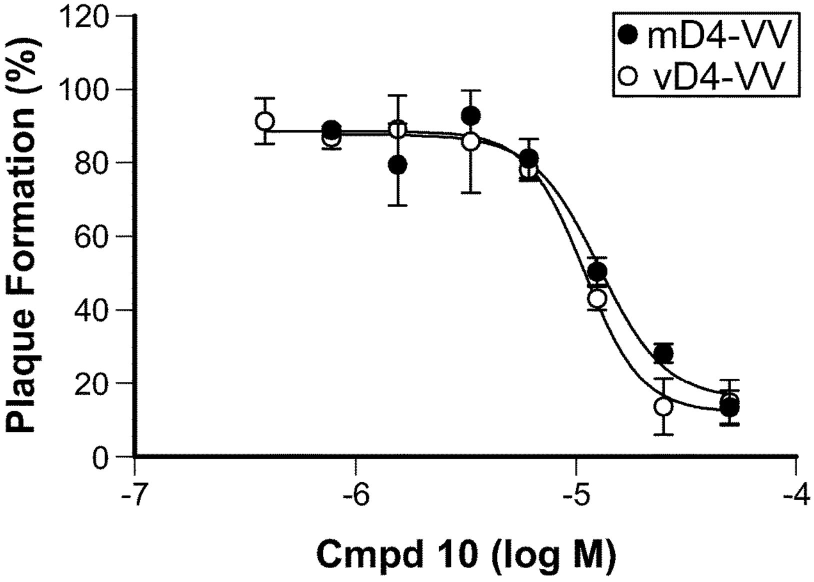
FIG. 7. Compound 10 inhibits mD4-VV hybrid virus replication. (A) Plaque reduction assay. Confluent BSC-1 cells were infected with mD4-VV hybrid virus or vD4-VV rescue virus (80 pfu/well) in the presence of increasing concentrations compound 10. After 16 h, cells were stained with crystal violet and plaques were counted. The mean EC50 of compound 10 obtained from two independent experiments is 14±SD 1 μM and 11±SD 1 μM for mD4-VV and vD4-VV, respectively. (B) Dot-blot hybridization. Confluent BSC-1 cells were infected with mD4-VV or vD4-VV (~1 MOI) in the absence or presence of 65 μM compound 10. Cells were collected at indicated time points and viral genomic DNA was extracted. Dot-blot hybridization was then performed using 32P-labeled vA20 DNA as a probe. The relative viral DNA levels are shown below each panel. None, no infection.

The mD4 inhibitor compound 10 blocks infection of the mD4-VV hybrid virus. As seen in the plaque reduction assay shown in FIG. 7A, compound 10 effectively blocked mD4-VV infection of BSC-1 cells with an $EC_{50}$=14 μM, which is comparable to its $IC_{50}$ of 28 μM in inhibiting processive DNA synthesis (FIG. 5B) and is far below its cytotoxicity $CC_{50}$ (175.4 μM) on BSC-1 cells as previously determined. In comparison, an $EC_{50}$=11 μM was obtained for compound 10 in inhibiting vD4-VV rescue virus (FIG. 7A). By contrast, the anti-herpesvirus drug acyclovir had no inhibitory effect, even at high concentrations (data not shown).

Figure 7B:
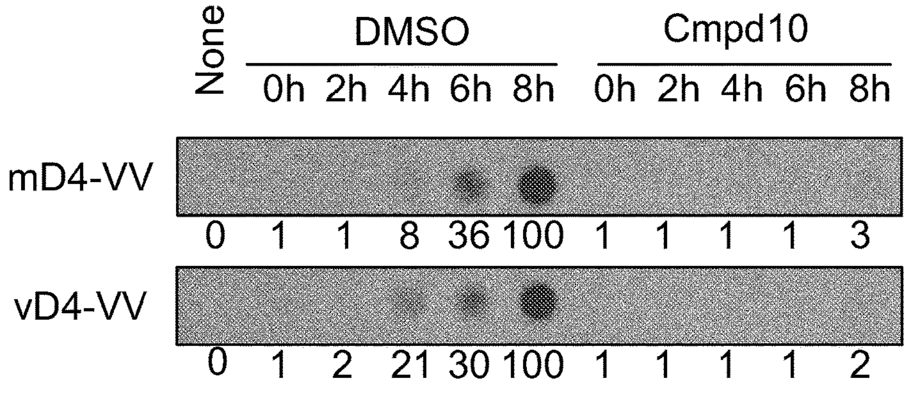

To confirm that compound 10 blocks mD4-VV replication via inhibiting viral processive DNA synthesis, its effect on viral DNA accumulation was evaluated throughout an infection time-course. As shown in FIG. 7B (upper row), treatment of BSC-1-infected cells with 65 μM compound 10 completely prevented mD4-VV genomic DNA accumulation at each time point of infection. By contrast, in the absence of compound 10 (DMSO alone), viral DNA was observed to accumulate over time as expected. A similar result was obtained with the control vD4-VV rescue virus (FIG. 7B, bottom row). These data clearly demonstrate that compound 10 inhibits viral DNA replication.

Discussion

There is no licensed antiviral drug available that specifically treats molluscum contagiosum (MC), a common viral skin infection that is prevalent in children and adults. Any attempts to identify compounds that might block MCV infection have been impeded by the inability to propagate this poxvirus in cell culture. In this study, a two-step strategy was devised to circumvent this roadblock. For the first-step, a novel and essential MCV target gene was identified that is inhibited in vitro by a small chemical compound. Specifically, the mD4 gene of MCV was cloned that is essential for processive DNA synthesis. It was showed that compound 10, previously demonstrated to be efficacious in blocking vaccinia poxvirus vD4, was capable of both binding mD4 and blocking mD4-dependent processive DNA synthesis as determined by in vitro assays. For the second-step, a vaccinia hybrid virus (mD4-VV) was constructed that substitutes the mD4 target gene for the natural vD4 gene. mD4-VV exhibited the same growth characteristics as the vD4-rescued vaccinia virus. Significantly, it was showed that compound 10 does indeed block the mD4-VV hybrid virus from replicating in cells. The fact that mD4 is required by the hybrid virus to be infectious and that mD4 is a physical and functional target of compound 10 predicts strongly that compound 10 will inhibit natural MCV infection. Importantly, this study provides for the first time, a systematic path for discovering drugs that specifically target MCV replication and infection.

Of the MCV processivity triad, only mD4 substituted for its vD4 counterpart in the in vitro processive DNA synthesis assay, whereas A20 and E9 substituted poorly (FIG. 2). This may be related to the fact that mD4 exhibits a greater chemical identity to its vaccinia virus counterpart (55%) than does its processivity partner A20 (30%). Significantly, purified mD4 can physically associate with both mA20 and vA20, as seen by pull-down assays, further validating the conservation of this poxvirus protein (FIG. 3B). Most importantly, compound 10 binds and inhibits mD4 function as shown here, as well as vD4. This suggests that compound 10 could bind to the conserved region of D4 that is involved in interacting with A20. Recently, the co-crystal structure of vD4 with the vA20 N-terminal domain revealed that the C-terminal residues 167-180 and 191-206 of vD4 are in direct contact with vA20. Point mutations of Arg167 and Pro173 in this region of vD4 were able to perturb formation of the D4/A20 complex. Sequence comparison of mD4 and vD4 indicates that the C-terminal region (residues 167-206 including Arg167 and Pro173) are conserved in D4 (67.5% identity, see FIG. 9A). It is notable that the predicted structure of mD4 superimposes directly onto the known crystal structure of vD4 (FIG. 9B). This may largely explain why both mD4 and vD4 are targeted by compound 10. Since D4 proteins of other poxviruses share high sequence identity with vD4 (-99%), compound 10 is anticipated to have broad-spectrum anti-poxviral activity. Notably, four other compounds that exhibited binding to vD4 by thermal shift (Nuth M, et al. 2011. *J. Med. Chem.* 54:3260-3267), failed to bind mD4 (this study, not shown), which may be accounted for by differences in their protein composition and local conformations. The mD4-VV viral hybrid system permits identification of additional compounds that directly bind and inhibit multiple regions of mD4, thus allowing the development of new therapeutics that specifically target MCV for treatment of MC.

In the invention of the present application, a novel antiviral target, the PF mD4, has been cloned and identified that can be inhibited by a small chemical compound to prevent the viral Pol from synthesizing extended strands of DNA. The type of MCV hybrid system described here can be exploited for discovering additional viral targets and compounds that will block infection.

Example 2

Binding of Compound 2 to mD4

Figure 10:
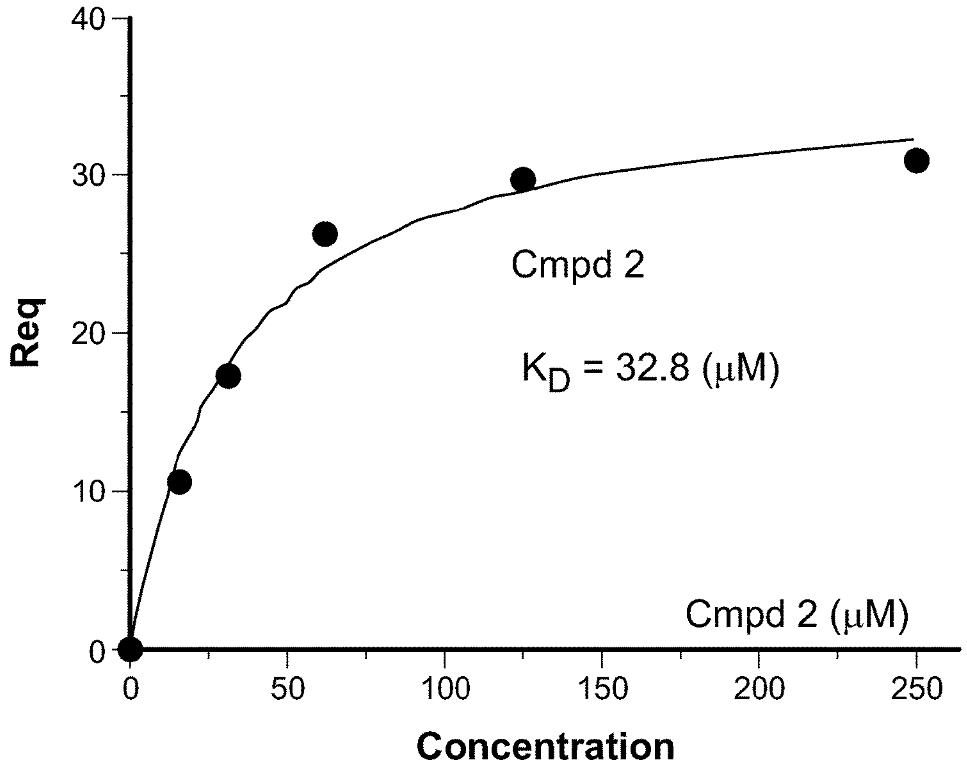
FIG. 10. The binding of compound 2 as follows

The binding of compound 2 to mD4 was determined by SPR. mD4 was immobilized onto a biosensor chip at ~3500 RU, and compound 2 was injected at 0-250 μM in buffer with 1% DMSO. The binding affinity $K_D$ was determined from the plot of steady-state response (Req) against compound 2 concentrations and fitting to a 1:1 binding model (FIG. 10).

Example 3

Antiviral Activity in 3-D Human Skin Organ Cultures

The 3-D System: MCV infection occurs exclusively in the skin, the 3-D Human Skin Organ Cultures are ideal to test a compound of the present invention such as compound 2 and other leads for antiviral activity against mD4-VV as well as to assay for stability and histopathology in the natural environment of its intended use. The 3-D cultures are prepared using acellular dermis as a supporting framework, to which are added stromal fibroblasts and epithelial cells (62). The postage-stamp size 3-D cultures (FIG. 11) are grown on trays with openings where they develop into human skin equivalents except for a blood supply (FIG. 12). All of the epidermal layers that include the cornified, granular, spinous and basal layers are formed above the dermal layer (FIG. 12).

mD4-VV infection and Compound 2 treatment of 3-D cultures: In a preliminary experiment, the 3-D culture (FIG. 11) was infected with the mD4-VV hybrid virus in the presence or absence of compound 2. Three days after infection, one-half of the 3-D cultures were harvested for viral titers and the other half for histology.

Viral Titer of mD4-VV was significantly reduced by compound 2 in the 3-D cultures. Specifically $10^6$ pfu of the mD4-VV hybrid virus in 80 μL of normal culture medium was dripped onto the top surface of each 3D-tissue. The tissues were incubated in 5 ml of the culture medium containing compound 2 or 0.5% DMSO as a drug vehicle. At 3 days post infection, the tissues were harvested and virus titers in each tissue were determined. As seen in FIG. 13, compound 2 caused a significant decline in the viral titer of mD4-VV compared to the DMSO drug vehicle alone. This agrees with results obtained in standard 2-D cultures.

Histological analysis reveals protection of the 3-D human skin organ culture by Compound 2. The other half of the 3-D cultures were examined histologically to assess the level of viral-induced tissue damage with and without compound 2. The 3-D tissues were cut in cross-section and H&E stained.

As seen in FIG. 14A, uninfected 3-D tissue treated with the DMSO had a normal appearing epidermis, which contained an abundant population of healthy stained keratinocytes. By contrast, as shown in FIG. 14B, infection of the 3-D culture with the mD4-VV virus caused eradication of the keratinocytes in the epidermal layer. However, when the 3-D culture was infected with mD4-VV and then directly treated with compound 2, an abundant population of stained keratinocytes was observed 3 days later in the epidermal layer. FIG. 14C. It is important to note that in separate experiments on 2-D keratinocyte cultures, compound 2 was not toxic at the concentrations used here. It is noteworthy that a somewhat similar 3-D human skin organ culture was previously used to examine acyclic nucleoside phosphonates (ANPs) related to cidofovir (Duraffour, et al. Antimicrob Agents Chemother. 51:4410-4419, 2007).

Table 1 provides $EC_{50}$ results for the compounds of the present invention (FIG. 15).

TABLE 1

| Cmpd No | Chemical Structure | $EC_{50}$ (mD4-VV) (μM) | Chemical Name |
|---|---|---|---|
| 1 | 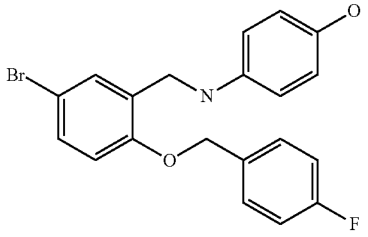 [SMILES: Oc1ccc(NCc2cc(Br)ccc2OCc2ccc(F)cc2)cc1] | 19.9 | 4-[[5-bromo-2-[(4-fluorophenyl)methoxy]phenyl]methylamino]phenol |
| 2 | 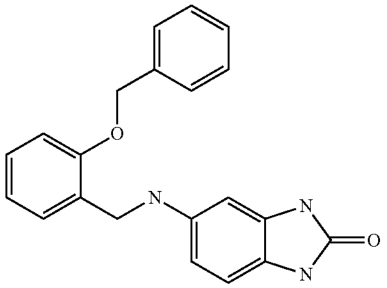 [SMILES: O=c1[nH]c2ccc(NCc3ccccc3OCc3ccccc3)cc2[nH]1] | 10.0 | 5-[(2-benzyloxyphenyl)methylamino]-1,3-dihydrobenzimidazol-2-one |
| 3 | 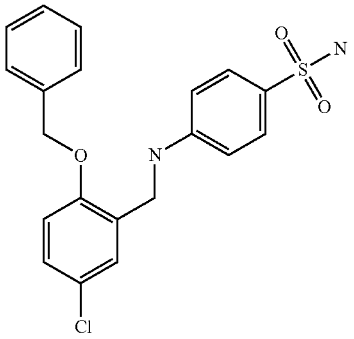 [SMILES: NS(=O)(=O)c1ccc(NCc2cc(Cl)ccc2OCc2ccccc2)cc1] | 13.9 | 4-[(2-benzyloxy-5-chloro-phenyl)methylamino]benzene-sulfonamide |

TABLE 1-continued
| Cmpd No | Chemical Structure | $EC_{50}$ (mD4-VV) (μM) | Chemical Name |
|---|---|---|---|
| 4 | 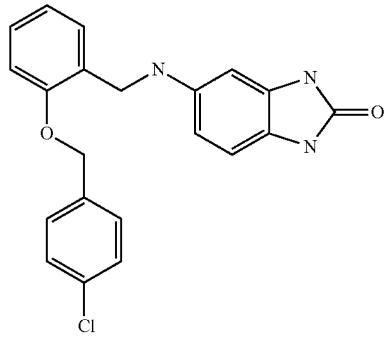 [SMILES: O=c1[nH]c2ccc(NCc3ccccc3OCc3ccc(Cl)cc3)cc2[nH]1] | 11.0 | 5-[[2-[(4-chlorophenyl)methoxy]phenyl] methylamino]-1,3-dihydrobenzimidazol-2-one |
| 5 | 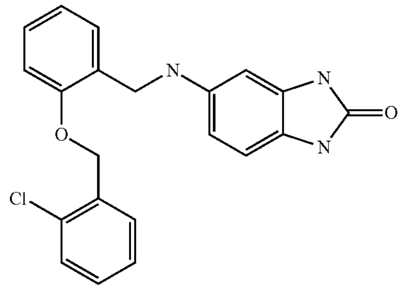 [SMILES: O=c1[nH]c2ccc(NCc3ccccc3OCc3ccccc3Cl)cc2[nH]1] | 14.9 | 5-[[2-[(2-chlorophenyl)methoxy]phenyl] methylamino]-1,3-dihydrobenzimidazol-2-one |
| 6 | 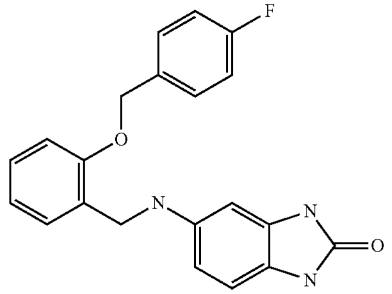 [SMILES: O=c1[nH]c2ccc(NCc3ccccc3OCc3ccc(F)cc3)cc2[nH]1] | 13.9 | 5-[[2-[(4-fluorophenyl)methoxy]phenyl] methylamino]-1,3-dihydrobenzimidazol-2-one |
| 7 | 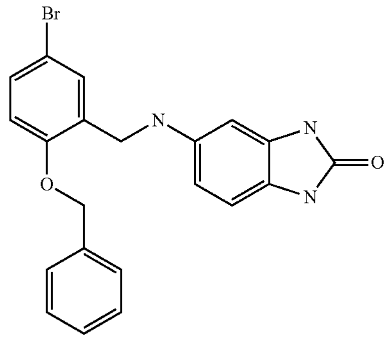 [SMILES: O=c1[nH]c2ccc(NCc3cc(Br)ccc3OCc3ccccc3)cc2[nH]1] | 11.0 | 5-[(2-benzyloxy-5-bromo-phenyl)methylamino]-1,3-dihydrobenzimidazol-2-one |

TABLE 1-continued
| Cmpd No | Chemical Structure | $EC_{50}$ (mD4-VV) (μM) | Chemical Name |
|---|---|---|---|
| 8 | 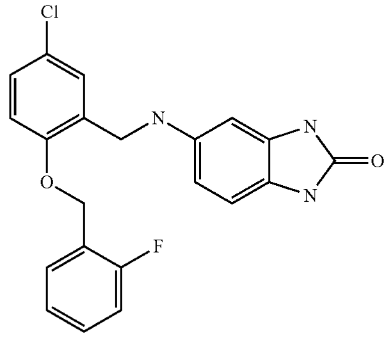 [SMILES: O=c1[nH]c2ccc(NCc3cc(Cl)ccc3OCc3ccccc3F)cc2[nH]1] | 11.0 | 5-[[5-chloro-2-[(2-fluorophenyl)methoxy]phenyl]methylamino]-1,3-dihydrobenzimidazol-2-one |
| 9 | 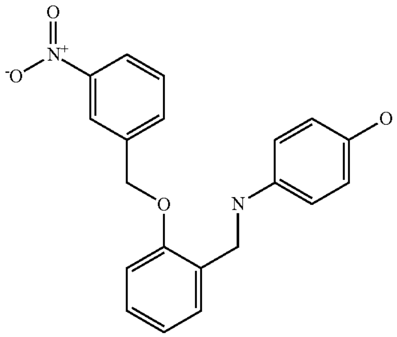 | 13.3 | 4-[[2-[(3-nitrophenyl)methoxy]phenyl]methylamino]phenol |
| 10 | 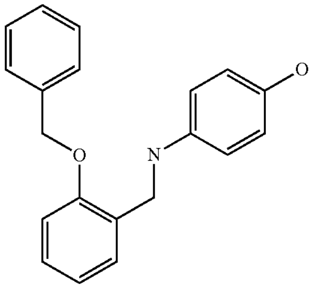 [SMILES: Oc1ccc(NCc2ccccc2OCc2ccccc2)cc1] | 35.6 | 4-[(2-benzyloxyphenyl)methylamino]phenol |
| 11 | 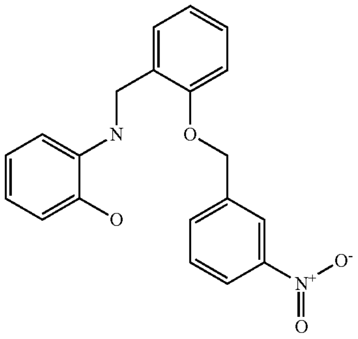 [SMILES: O=[N+]([O-])c1cccc(COc2ccccc2CNc2ccccc2O)c1] | 17.7 | 2-[[2-[(3-nitrophenyl)methoxy]phenyl]methylamino]phenol |

TABLE 1-continued

| Cmpd No | Chemical Structure | $EC_{50}$ (mD4-VV) (μM) | Chemical Name |
|---|---|---|---|
| 12 | 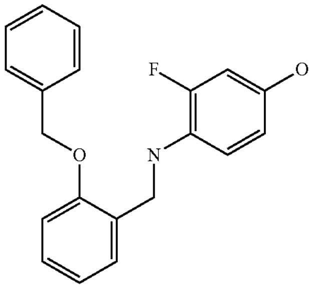 [SMILES: Oc1ccc(NCc2ccccc2OCc2ccccc2)c(F)c1] | 19.4 | 4-[(2-benzyloxyphenyl)methylamino]-3-fluoro-phenol |
| 13 | 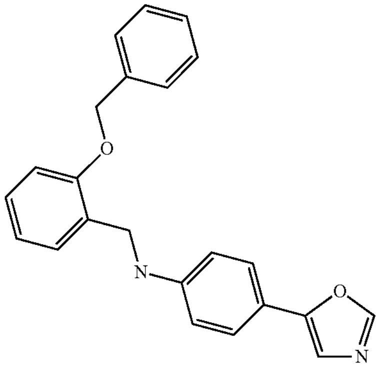 [SMILES: c1ccc(COc2ccccc2CNc2ccc(-c3cnco3)cc2)cc1] | 14.4 | N-[(2-benzyloxyphenyl)methyl]-4-oxazol-5-yl-aniline |
| 14 | 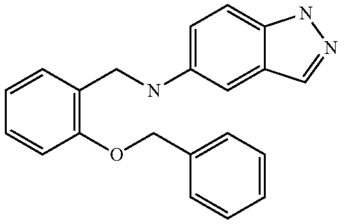 [SMILES: c1ccc(COc2ccccc2CNc2ccc3[nH]ncc3c2)cc1] | 7.9 | N-[(2-benzyloxyphenyl)methyl]-1H-indazol-5-amine |

The compound of the present invention such as compound 2 shows the attributes including specific blocking processive DNA synthesis in vitro; near nM potency of blocking mD4-VV viral infection ($EC_{50}$=3 μM), and its antiviral activity in the 3-D human skin organ culture. Further, compound 2 has a cellular toxicity with a $CC_{50}$>100; a half-life stability in mouse liver microsomes of 36 min which is a greater than 5-fold increase above the 6.7 min half-life of compound 10 in mouse liver microsomes; a measurable $K_D$=32.8 μM derived from compound 2 binding to mD4 protein by SPR (Surface Plasmon Resonance) (FIG. 10).

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A compound of formula (X) or (XII):

(X)

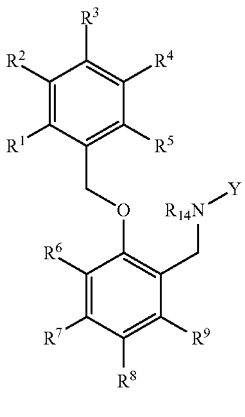

-continued (XII)

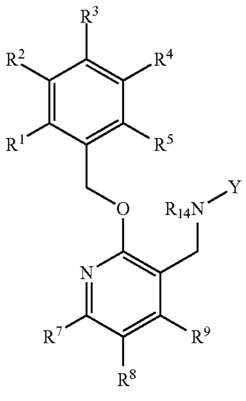

wherein:

Y is heteroaryl; which is substituted with at least one group selected from the group consisting of phenyl and heteroaryl;

$R^1$, $R^2$, $R^3$, $R^4$, $R^5$, $R^6$, $R^7$, $R^8$, and $R^9$ are independently selected from the group consisting of H, $C_1$-$C_6$ alkyl, halo, cyano, nitro, $SO_2NH_2$, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl; or two adjacent $OR^a$ or $NR'''R''$ groups, together with the atoms to which they are attached, form a 5-7 membered heterocycloalkyl group;

$R^{14}$ is H, $C_1$-$C_3$ alkyl, $C(O)OR^a$, $C(O)R^b$, $C(O)NR'''R''$, $SOR^b$, or $SO_2R^b$;

$R^a$ and $R^b$ are each independently selected from the group consisting of H, $C_1$-$_6$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;

$R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 3-7 membered heterocycloalkyl group;

each occurrence of aryl is independently selected from the group consisting of phenyl and naphthyl; and each occurrence of heteroaryl is independently selected from the group consisting of pyridine, pyrimidine, pyrazine, indole, indolizine, benzimidazole, 1,3-dihydrobenzimidazol-2-one, and indazole.

2. The compound of claim 1, wherein $R^1$, $R^2$, $R^3$, $R^4$, $R^5$, $R^6$, $R^7$, $R^8$, and $R^9$ are each independently selected from the group consisting of H, halo, cyano, nitro, $CF_3$, and $SO_2NH_2$.

3. The compound of claim 1, wherein Y is pyridine.

4. The compound of claim 1, wherein $R^{14}$ is H or $C_1$-$C_3$ alkyl.

5. The compound of claim 1, wherein Y is substituted with at least one heteroaryl.

6. A compound selected from the group consisting of:

5-[(2-benzyloxyphenyl)methylamino]-1,3-dihydrobenzimidazol-2-one,

5-[[2-[(4-chlorophenyl)methoxy]phenyl]methylamino]-1,3-dihydrobenzimidazol-2-one, 5-[[2-[(2-chlorophenyl)methoxy]phenyl]methylamino]-1,3-dihydrobenzimidazol-2-one, 5-[[2-[(4-fluorophenyl)methoxy]phenyl]methylamino]-1,3-dihydrobenzimidazol-2-one, 5-[(2-benzyloxy-5-bromo-phenyl)methylamino]-1,3-dihydrobenzimidazol-2-one, 5-[[5-chloro-2-[(2-fluorophenyl)methoxy]phenyl]methylamino]-1,3dihydrobenzimidazol-2-one, N-[(2-benzyloxyphenyl)methyl]-1H-indazol-5-amine, 4-[[5-bromo-2-[(4-fluorophenyl)methoxy]phenyl]methylamino]phenol, 4-[(2-benzyloxy-5-chloro-phenyl)methyl amino]benzene sulfonamide, 4-[(2-benzyloxy-5-chloro-phenyl)methyl amino]benzene sulfonamide, 4-[[2-[(3-nitrophenyl)methoxy]phenyl]methyl amino] phenol, 2-[[2-[(3-nitrophenyl)methoxy]phenyl]methyl amino] phenol, 4-[(2-benzyloxyphenyl)methylamino]-3-fluoro-phenol, or N-[(2-benzyloxyphenyl)methyl]-4-oxazol-5-yl-aniline;

or a salt thereof.

7. A pharmaceutical composition comprising the compound of claim 6, or a pharmaceutically acceptable salt thereof, and at least one pharmaceutically acceptable carrier.

8. A method of inhibiting, treating, or abrogating a molluscum contagiosum virus infection in a subject in need thereof, the method comprising administering to said subject a therapeutically effective amount of a compound of formula (IX), or a pharmaceutically acceptable salt thereof:

(IX)

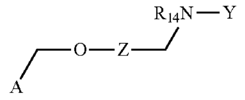

wherein:

A, Z, and Y is aryl or heteroaryl, each optionally substituted with $C_1$-$C_6$ alkyl, halo, cyano, nitro, $C_1$-$C_6$ haloalkyl, $OR^a$, $SR^a$ $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, or heteroarylalkyl; or two adjacent $OR^a$ or $NR'''R''$ groups, together with the atoms to which they are attached, form a 5-7 membered heterocycloalkyl group;

$R^{14}$ is H, $C_1$-$C_3$ alkyl, $C(O)OR^a$, $C(O)R^b$, $C(O)NR'''R''$, $SOR^b$, or $SO_2R^b$;

$R^a$ and $R^b$ are each independently selected from the group consisting of H, $C_{1-6}$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl; and $R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 3-7 membered heterocycloalkyl group.

9. The method of claim 8, wherein the compound is a compound of formula (X) or (XII):

(X)

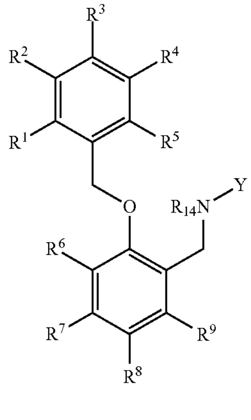

-continued (XII)

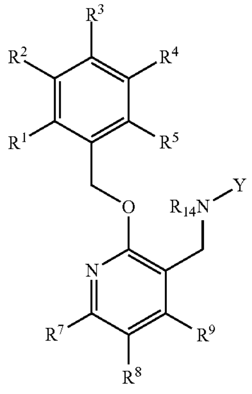

wherein:

Y is heteroaryl; and $R^1$, $R^2$, $R^3$, $R^4$, $R^5$, $R^6$, $R^7$, $R^8$, and $R^9$ are independently selected from the group consisting of H, $C_1$-$C_6$ alkyl, halo, cyano, nitro, $SO_2NH_2$, $C_1$-$C_6$ haloalkyl, $OR^a$, $SR^a$ $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl; or two adjacent $OR^a$ or $NR'''R''$ groups, together with the atoms to which they are attached, form a 5-7 membered heterocycloalkyl group.

10. The method of claim 9, wherein Y is pyridine, pyrimidine, pyrazine, indole, indolizine, benzimidazole, 1,3-dihydrobenzimidazol-2-one, or indazole.

11. The method of claim 9, wherein the compound is a compound of formula (XI):

(XI)

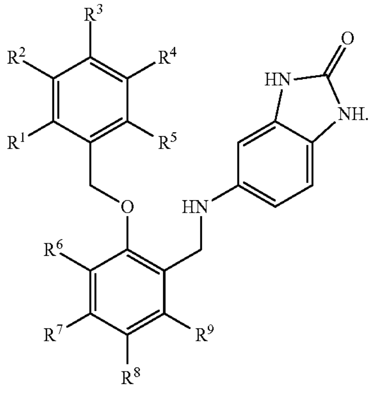

12. The method of claim 8, wherein the compound is a compound of formula (XIII) or (XIV):

(XIII)

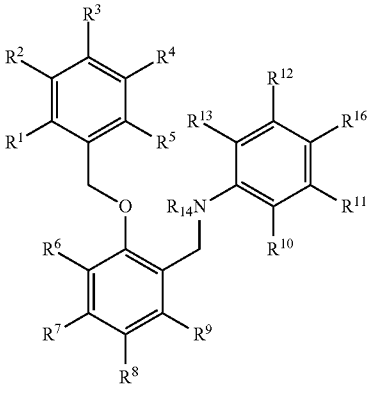

(XIV)

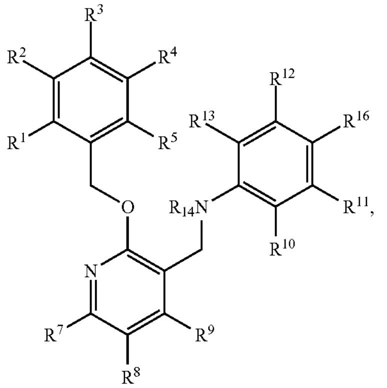

wherein:

$R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{16}$ are independently selected from the group consisting of H, $C_1$-$C_6$ alkyl, halo, cyano, nitro, $SO_2NH_2$, $C_1$-$C_6$ haloalkyl, $OR^a$, $SR^a$ $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl; or two adjacent $OR^a$ or $NR'''R''$ groups, together with the atoms to which they are attached, form a 5-7 membered heterocycloalkyl group.

13. A method of inhibiting, treating, or abrogating a molluscum contagiosum virus infection in a subject in need thereof, the method comprising administering to said subject a therapeutically effective amount of a compound selected from the group consisting of:

5-[(2-benzyloxyphenyl)methylamino]-1,3-dihydrobenzimidazol-2-one,

5-[[2-[(4-chlorophenyl)methoxy]phenyl]methylamino]-1,3-dihydrobenzimidazol-2-one, 5-[[2-[(2-chlorophenyl)methoxy]phenyl]methylamino]-1,3-dihydrobenzimidazol-2-one, 5-[[2-[(4-fluorophenyl)methoxy]phenyl]methylamino]-1,3-dihydrobenzimidazol-2-one, 5-[(2-benzyloxy-5-bromo-phenyl)methylamino]-1,3-dihydrobenzimidazol-2-one, 5-[[5-chloro-2-[(2-fluorophenyl)methoxy]phenyl]methylamino]-1,3-dihydrobenzimidazol-2-one, N-[(2-benzyloxyphenyl)methyl]-1H-indazol-5-amine, 4-[[5-bromo-2-[(4-fluorophenyl)methoxy]phenyl]methylamino]phenol, 4-[(2-benzyloxy-5-chloro-phenyl)methylamino]benzenesulfonamide, 4-[[2-[(3-nitrophenyl)methoxy]phenyl]methylamino]phenol, 2-[[2-[(3-nitrophenyl)methoxy]phenyl]methylamino]phenol, 4-[(2-benzyloxyphenyl)methylamino]phenol, 4-[(2-benzyloxyphenyl)methylamino]-3-fluoro-phenol, or N-[(2-benzyloxyphenyl)methyl]-4-oxazol-5-yl-aniline; or a salt thereof.

14. A method of inhibiting, treating, or abrogating a molluscum contagiosum virus infection in a subject in need thereof, the method comprising administering to said subject a therapeutically effective amount of a compound of formula (I), or a pharmaceutically acceptable salt thereof:

(I)

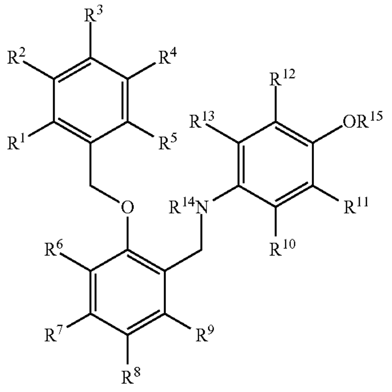

wherein:

$R^{14}$ is H, $C_1$-$C_3$ alkyl, $C(O)OR^a$, $C(O)R^b$, $C(O)NR'''R''$, $SOR^b$, or $SO_2R^b$;

$R^{15}$ is H, $C_1$-$C_5$ alkyl, $C(O)R^a$, or $C(O)NR'''R''$;

$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from the group consisting of H, $C_1$-$C_6$ alkyl, halo, cyano, nitro, $SO_2NH_2$, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_1$-$C_6$ alkyl, $C_1$-$C_6$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;

$R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 3-7 membered heterocycloalkyl group.

15. The method of claim 14, wherein the compound is selected from the group consisting of a compound of formula (II):

(II)

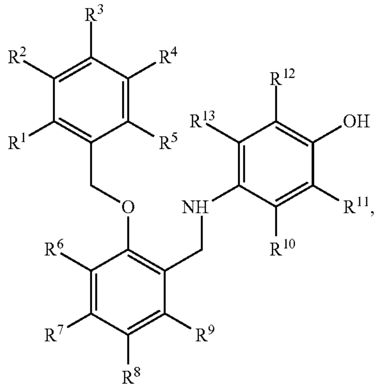

a compound of formula (III):

(III)

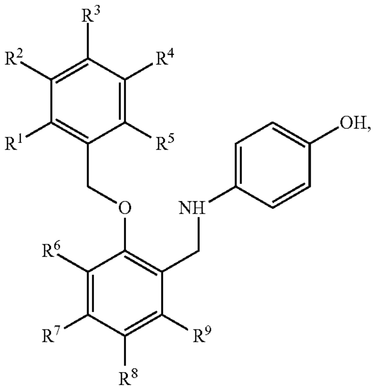

a compound of formula (IV):

(IV)

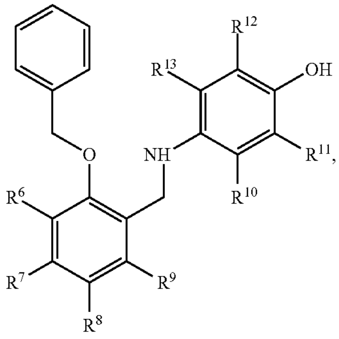

a compound of formula (V):
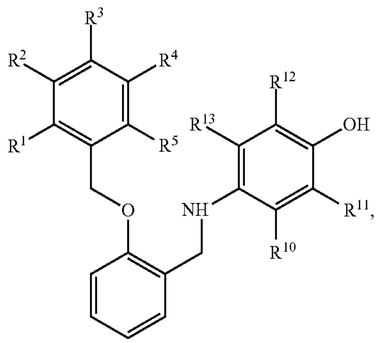
(V)
a compound of formula (VI):
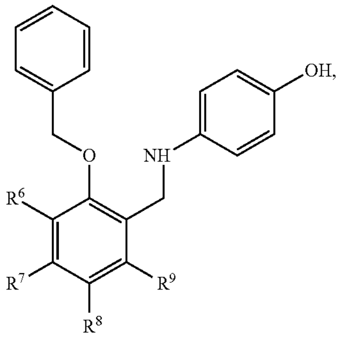
(VI)
a compound of formula (VII):
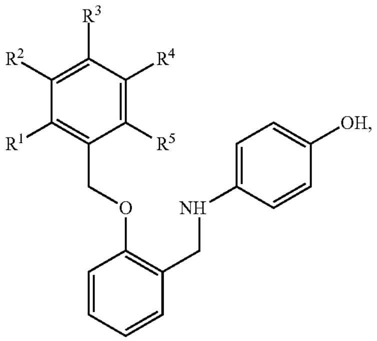
(VII)
and
a compound of formula (VIII):
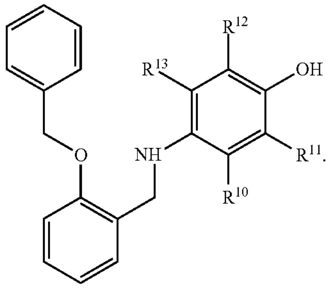
(VIII)
16. The method of claim 8, wherein the compound is administered topically to the subject.
* * * * *

UNITED STATES PATENT AND TRADEMARK OFFICE

CERTIFICATE OF CORRECTION

PATENT NO. : 10,112,895 B2
APPLICATION NO. : 15/515534
DATED : October 30, 2018
INVENTOR(S) : Robert P. Ricciardi et al.

It is certified that error appears in the above-identified patent and that said Letters Patent is hereby corrected as shown below:

In the Specification

On Column 1, Line 19, after "STATEMENT REGARDING FEDERALLY SPONSORED RESEARCH OR DEVELOPMENT", please replace the existing paragraph with the following paragraph:
-- This invention was made with government support under grant numbers AI082211, AR057217, AI113952, AI125005, and AI115759 awarded by the National Institutes of Health. The government has certain rights in the invention. --

Signed and Sealed this
Thirtieth Day of July, 2019

Andrei Iancu
*Director of the United States Patent and Trademark Office*

SEQUENCE LISTING

<160> NUMBER OF SEQ ID NOS: 12

<210> SEQ ID NO 1
<211> LENGTH: 32
<212> TYPE: DNA
<213> ORGANISM: Artificial Sequence
<220> FEATURE:
<223> OTHER INFORMATION: chemically synthesized

<400> SEQUENCE: 1
agaaagcttg ccatggagat ccggtgtctc aa 32

<210> SEQ ID NO 2
<211> LENGTH: 34
<212> TYPE: DNA
<213> ORGANISM: Artificial Sequence
<220> FEATURE:
<223> OTHER INFORMATION: chemically synthesized

<400> SEQUENCE: 2
tctctctaga ctagttcgag aagacggggc gcac 34

<210> SEQ ID NO 3
<211> LENGTH: 31
<212> TYPE: DNA
<213> ORGANISM: Artificial Sequence
<220> FEATURE:
<223> OTHER INFORMATION: chemically synthesized

<400> SEQUENCE: 3
gagaaagctt gccatggcca aggagcccga t 31

<210> SEQ ID NO 4
<211> LENGTH: 29
<212> TYPE: DNA
<213> ORGANISM: Artificial Sequence
<220> FEATURE:
<223> OTHER INFORMATION: chemically synthesized

<400> SEQUENCE: 4
tctctctaga ttacttctcg gcgctggac 29

<210> SEQ ID NO 5
<211> LENGTH: 33
<212> TYPE: DNA
<213> ORGANISM: Artificial Sequence
<220> FEATURE:
<223> OTHER INFORMATION: chemically synthesized

<400> SEQUENCE: 5
gagaaagctt gccatggtgc gcgagcgcgc gct 33

<210> SEQ ID NO 6
<211> LENGTH: 25
<212> TYPE: DNA
<213> ORGANISM: Artificial Sequence
<220> FEATURE:
<223> OTHER INFORMATION: chemically synthesized

<400> SEQUENCE: 6
tctctctaga ggggtacgaa gccct 25

<210> SEQ ID NO 7
<211> LENGTH: 27
<212> TYPE: DNA
<213> ORGANISM: Artificial Sequence
<220> FEATURE:
<223> OTHER INFORMATION: chemically synthesized

<400> SEQUENCE: 7
agacatatgc tgcgcgagcg cgcgctg 27

<210> SEQ ID NO 8
<211> LENGTH: 29
<212> TYPE: DNA
<213> ORGANISM: Artificial Sequence
<220> FEATURE:
<223> OTHER INFORMATION: chemically synthesized -continued

<400> SEQUENCE: 8
agaggatcct aaaggggtac gaagccctg 29

<210> SEQ ID NO 9
<211> LENGTH: 31
<212> TYPE: DNA
<213> ORGANISM: Artificial Sequence
<220> FEATURE:
<223> OTHER INFORMATION: chemically synthesized

<400> SEQUENCE: 9
gtggaattca atgctgcgcg agcgcgcgct g 31

<210> SEQ ID NO 10
<211> LENGTH: 30
<212> TYPE: DNA
<213> ORGANISM: Artificial Sequence
<220> FEATURE:
<223> OTHER INFORMATION: chemically synthesized

<400> SEQUENCE: 10
gagaagcttc taaaggggta cgaagccctg 30

<210> SEQ ID NO 11
<211> LENGTH: 19
<212> TYPE: DNA
<213> ORGANISM: Artificial Sequence
<220> FEATURE:
<223> OTHER INFORMATION: chemically synthesized

<400> SEQUENCE: 11
tataatgaat tcaatgctg 19

<210> SEQ ID NO 12
<211> LENGTH: 45
<212> TYPE: DNA
<213> ORGANISM: Artificial Sequence
<220> FEATURE:
<223> OTHER INFORMATION: chemically synthesized

<400> SEQUENCE: 12
aaaggtatct aatttgatat aataaagcca tgctgcgcga gcgcg 45